United States Patent [19]

Sawayama et al.

[11] Patent Number: 4,826,814

[45] Date of Patent: May 2, 1989

[54] TRIPEPTIDE DERIVATIVES

[75] Inventors: Tadahiro Sawayama, Kawanishi; Masatoshi Tsukamoto, Settsu; Takashi Sasagawa, Ikeda; Kazuya Nishimura, Osaka; Kanoo Hosoki, Toyonaka; Kunihiko Takeyama, Ikoma, all of Japan

[73] Assignee: Dainippon Pharmaceutical Co., Ltd., Osaka, Japan

[21] Appl. No.: 46,189

[22] Filed: May 5, 1987

[30] Foreign Application Priority Data

May 9, 1986 [JP] Japan ................................. 61-107394
Jul. 3, 1986 [JP] Japan ................................. 61-156693
Jan. 26, 1987 [JP] Japan ................................. 62-16361

[51] Int. Cl.[4] ....................... A61K 37/43; C07K 5/08
[52] U.S. Cl. ....................................... 514/18; 530/331
[58] Field of Search ................... 530/316, 331; 514/18

[56] References Cited

U.S. PATENT DOCUMENTS

| | | | |
|---|---|---|---|
| 4,215,110 | 7/1980 | Lotti et al. ............................. | 514/18 |
| 4,548,926 | 10/1985 | Matsueda et al. ..................... | 514/18 |
| 4,590,178 | 5/1986 | Sakakibara et al. ................... | 514/18 |
| 4,616,002 | 10/1986 | Kamber et al. ........................ | 514/18 |
| 4,678,800 | 7/1987 | Stanton et al. ....................... | 514/333 |

Primary Examiner—Delbert R. Phillips
Attorney, Agent, or Firm—Wenderoth, Lind & Ponack

[57] ABSTRACT

There are provided tripeptide compounds represented by the following formula

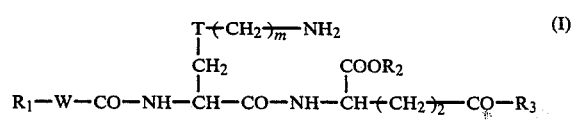

wherein $R_1$ represents a $C_{1-10}$ alkyl group, a $C_{4-7}$ cycloalkyl or $C_{5-7}$ cycloalkyl-lower alkyl group, a phenyl or phenyl-lower alkyl group in which the benzene ring may optionally be substituted by a substituent selected from halogen, lower alkyl, lower alkoxy, phenyl, methylenedioxy, ethylenedioxy, amino, di(lower alkyl)amino and hydroxy, a naphthyl or naphthyl-lower alkyl group in which the naphthalene ring may optionally be substituted by a substituent selected from halogen, lower alkyl, lower alkoxy and hydroxy, a heterocyclic or heterocyclic-lower alkyl group in which the heterocycle is a saturated or unsaturated 5- or 6-membered ring containing a nitrogen, oxygen or sulfur atom as the hetero atom, and may optionally be substituted by a substituent selected from halogen, lower alkyl, lower alkoxy, amino, di(lower alkyl)amino, hydroxy, oxo and saturated 5- or 6-membered nitrogen-containing heterocyclic group, and further may optionally be fused to a benzene ring, or an imidazolylvinyl group; $R_2$ represents a hydrogen atom, a $C_{1-10}$ alkyl group or a benzyl group; $R_3$ represents a group of the formula

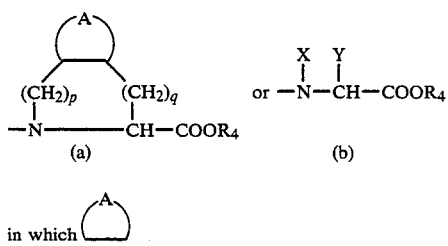

in which

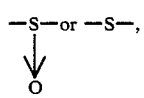

represents a benzene, cyclopentane or cyclohexane ring, $R_4$ represents a hydrogen atom, a $C_{1-10}$ alkyl group or a benzyl group, p is 0 or 1, q is 1, 2, or 3, and X represents a phenyl group which may optionally be substituted by a substituent selected from halogen, lower alkoxy and hydroxy, a $C_{4-8}$ cycloalkyl group, or a $C_{5-7}$ cycloalkyl group which is fused to a benzene, and Y represents a hydrogen atom or a lower alkyl group, or X and Y, together with the nitrogen and carbon atoms to which they are bonded, forms a 5- or 6-membered heterocycle which may contain a nitrogen, oxygen or sulfur atom, W represents a single bond, —O— or —NH—, T represents a single bond, $$-\overset{\downarrow}{\underset{O}{S}}- \text{ or } -S-,$$

and m is 2 or 3, or salts thereof and processes for production thereof. The compounds are useful as antihypertensive agents.

17 Claims, No Drawings

TRIPEPTIDE DERIVATIVES

This invention relates to tripeptide derivatives, and more specifically, to tripeptide derivatives represented by the following formula

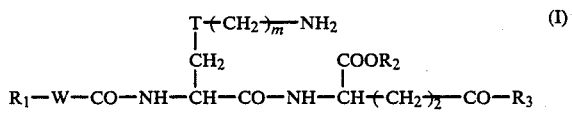

wherein $R_1$ represents a $C_{1-10}$ alkyl grup, a $C_{4-7}$ cycloalkyl or $C_{5-7}$ cycloalkyl-lower alkyl group, a phenyl or phenyl-lower alkyl group in which the benzene ring may optionally be substituted by a substituent selected from halogen, lower alkyl, lower alkoxy, phenyl, methylenedioxy, ethylenedioxy, amino, di(lower alkyl)amino and hydroxy, a naphthyl or naphthyl-lower alkyl group in which the naphthalene ring may optionally be substituted by a substituent selected from halogen, lower alkyl, lower alkoxy and hydroxy, a heterocyclic or heterocyclic-lower alkyl group in which the heterocycle is a saturated or unsaturated 5- or 6-membered ring containing a nitrogen, oxygen or sulfur atom as the hetero atom, and may optionally be substituted by a substituent selected from halogen, lower alkyl, lower alkoxy, amino, di(lower alkyl)amino, hydroxy, oxo and saturated 5- or 6-membered nitrogen-containing heterocyclic group, and further may optionally be fused to a benzene ring, or an imidazolylvinyl group; $R_2$ represents a hydrogen atom, a $C_{1-10}$ alkyl group or a benzyl group; $R_3$ represents a group of the formula

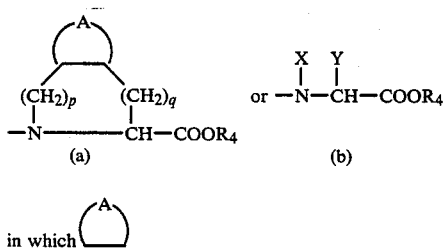

in which $\overset{A}{\bigcirc}$ represents a benzene, cyclopentane or cyclohexane ring, $R_4$, represents a hydrogen atom, a $C_{1-10}$ alkyl group or a benzyl group, p is 0 or 1, q is 1, 2, or 3, and X represents a phenyl group which may optionally be substituted by a substituent selected from halogen, lower alkoxy and hydroxy, a $C_{4-8}$ cycloalkyl group, or a $C_{5-7}$ cycloalkyl group which is fused to a benzene, and Y represents a hydrogen atom or a lower alkyl group, or X and Y, together with the nitrogen and carbon atoms to which they are bonded, forms a 5- or 6-membered heterocycle which may contain a nitrogen, oxygen or sulfur atom,
W represents a single bond, —O— or —NH—, T represents a single bond, $$-S-\text{ or }-\underset{\underset{O}{\downarrow}}{S}-,$$

and m is 2 or 3, or salts thereof; processes for production thereof; and the use thereof as a medicine, particularly an antihypertensive agent.

As compounds structurally similar to the tripeptide derivatives of formula (I) above, G. M. Ksander et al. discloses 1-(L-lysyl-gamma-D-glutamyl)indoline-2(S)-carboxylic acid and 1-($N^2,N^6$-dibenzyloxycarbonyl-L-lysyl-gamma-D-glutamyl)indoline-2(S)-carboxylic acid as angiotensin converting enzyme (ACE) inhibitors (Journal of Medicinal Chemistry, 1985, vol. 28, No. 11, pages 1606–1611). This publication states that these known compounds show in vitro inhibition of ACE. Our investigations have shown however that in an in vivo test with rats, these known compounds do not show any significant antihypertensive action after oral administration.

The tripeptide derivatives of formula (I) provided by this invention are novel compounds which are structurally different from the above known compounds in that the amino group at the $N^2$-position of the basic amino acid moiety is mono-substituted by a specific substituent and the amino group at the $N^6$-position is unsubstituted. Furthermore, it is quite unexpected from the above known compounds that the tripeptide derivatives of formula (I) or salts thereof provided by this invention have not only ACE inhibiting activity but also excellent antihypertensive activity in oral administration unlike the known compounds. Accordingly, the tripeptide derivatives of formula (I) and salts thereof in accordance with this invention can be used as medicines, particularly antihypertensive agents.

The term "lower", used in the present specification and the appended claims to qualify a group or a compound, means that the group or compound so qualified has not more than 5, preferably not more than 3, carbon atoms.

The alkyl group may be linear or branched. The "$C_{1-10}$ alkyl group" includes methyl, ethyl, n-propyl, isopropyl, n-butyl, sec-butyl, tert-butyl, isobutyl, n-hexyl, n-octyl and n-decyl. Methyl and ethyl are preferred as the "lower alkyl group". Examples of the "lower alkoxy group" include methoxy, ethoxy, tert-butoxy and n-pentyloxy.

The "$C_{4-7}$ cycloalkyl group" includes cyclobutyl, cyclopentyl, cyclohexyl and cycloheptyl. Examples of the "$C_{5-7}$ cycloalkyl-lower alkyl group" are cyclopentylmethyl, cyclohexylmethyl, cyclohexylethyl and cycloheptylmethyl.

The "halogen" includes fluorine, chlorine, bromine and iodine, and chlorine and fluorine are preferred. Specific examples of the "di(lower alkyl)amino" are dimethylamino, diethylamino and methylethylamino.

Examples of the "phenyl-lower alkyl group" are benzyl and phenehyl. The benzene ring in the "phenyl" and "phenyl-lower alkyl" groups may optionally be substituted by 1 to 4, preferably 1 to 3, substituents selected from halogen, lower alkyl, lower alkoxy, phenyl, methylenedioxy, ethylenedioxy, amino, di(lower alkyl)amino and hydroxy. Examples of substituted phenyl and phenyl-lower alkyl groups include 4-chlorophenyl, 4-fluorophenyl, 4-methylphenyl, 2-methylphenyl, 4-isopropylphenyl, 2-methyl-6-hydroxyphenyl, 2-methoxyphenyl, 4-methoxyphenyl, 3-methoxy-4-hydroxyphenyl, 3,5-dimethoxy-4-hydroxyphenyl, 4-phenylphenyl, 3,4-ethylenedioxyphenyl, 3-amino-4-hydroxyphenyl, 4-dimethylaminophenyl, 4-hydroxyphenyl, 2-hydroxyphenyl, 4-chlorobenzyl, 2-fluorobenzyl, 2-chlorobenzyl, 4-methylbenzyl, 2- methylbenzyl, 4-methoxyphenethyl, 4-phenylbenzyl, 3,4-methylenedioxybenzyl, and 4-hydroxyphenethyl.

Examples of the "naphthyl-lower alkyl group" are alpha-naphthylmethyl and alpha-naphthylethyl, and the naphthalene ring in the "naphthyl group" and "naphthyl-lower alkyl group" may optionally be substituted by 1 to 3, preferably 1 or 2, substituents selected from halogen, lower alkyl, lower alkoxy and hydroxy. Examples of the substituted "naphthyl" and "naphthyl-lower alkyl" groups are 3-hydroxynaphthalen-2-yl, 6-hydroxynaphthalen-2-yl, 3-methylnaphthalen-1-yl methyl, and 6-methoxynaphthalen-1-yl ethyl.

The "saturated or unsaturated 5- or 6-membered heterocyclic group containing a nitrogen, oxygen or sulfur atom as the hetero atom" may include 1 to 3 such hetero atoms, and specific examples include 2-furyl, 2-pyrrolidinyl, 3-pyridyl, 2-pyridyl, 4-pyridyl, 2-thienyl and 2-pyrazinyl. Examples of the "heterocyclic-lower alkyl group" include 2-pyridylethyl, 3-pyridylmethyl and morpholinoethyl.

The heterocycle in these "heterocyclic" and "heterocyclic-lower alkyl" groups may optionally be substituted by 1 to 3, preferably 1 or 2, substituents selected from halogen, lower alkyl, lower alkoxy, amino, di(-lower alkyl)amino, hydroxy, oxo and saturated 5- or 6-membered nitrogen-containing heterocyclic group (examples of this nitrogen-containing heterocyclic group are 1-pyrrolidinyl and morpholino). Examples of such substituted heterocyclic or heterocyclic-lower alkyl groups include 2-chloropyridin-5-yl, 2-chloropyridin-3-yl, 2-methylpyridin-5-yl, 2-methoxypyridin-5-yl, 2-ethoxypyridin-5-yl, 2-n-propyloxypyridin-5-yl, 2-isopropoxypyridin-5-yl, 2-aminopyridin-5-yl, 2-dimethylaminopyridin-5yl, 2-hydroxypyridin-5-yl, 2-pyrrolidon-5-yl, 2-pyrrolidinylpyridin-5-yl, 2-morpholinopyridin-5-yl, 3-hydroxypyridin-2-ylmethyl, 3-methoxypyridin-2-ylmethyl, 2-chloropyridin-6-ylmethyl and 2-methylpyridin-6-ylmethyl. A benzene ring may optionally be fused to the above heterocycle. Examples of such a fused ring are qunolin-3-yl, indolin-2-yl, thianaphthen-2-yl, quinoxalin-2-yl, and isoquinolin-2-yl.

Specific examples of the group of formula (a) as the group $R_3$ in formula (I) include 2(S)-carboxyindolinyl, 2-carboxy(2S,3aS,7aS)octahydro-indolyl, 1,2,3,4-tetrahydroisoquinolin-3-carboxylic acid-2-yl and cis, endo-2-azabicyclo[3.3.0]octan-3-carboxylic acid-2-yl.

Specific examples of the group of formula (b) as the group $R_3$ include N-(4-methoxyphenyl)alanino, L-prolino, N-cyclooctylglycino, N-cyclopenthlglycino, and thiazolidin-4-carboxylic acid-3-yl.

In general formula (I), W preferably represents a single bond or —O—, and T preferably represents a single bond. Generally, both $R_2$ and $R_4$ are preferably hydrogen atoms. Preferably, $R_3$ represents the group of formula (a) in which

is a benzene or cyclohexane ring, p is 0, and q is 1.

A preferred group of the tripeptride derivatives (I) provided by this invention are represented by the following formula

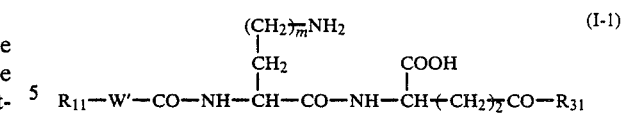

wherein $R_{11}$—W'— represents a $C_{4-7}$ cycloalkyl, $C_{4-7}$ cycloalkyloxy, cyclohexylmethyloxy or cyclohexylethyloxy group, a phenyl group which may optionally be substituted by 1 to 4 substituents (preferably 1 substituent) selected from lower alkoxy, halogen and hydroxy, a benzyloxy or phenethyloxy group in which the benzene ring may optionally be substituted by 1 to 4 substituents (preferably 1 substituent) selected from lower alkoxy, methylenedioxy and hydroxy, a pyridyl group which may optionally be substituted, preferably at the 2-or 6-position, by a substituent selected from halogen, lower alkoxy, methyl and dimethylamino, a pyridylmethyloxy or pyridylethyloxy group in which the pyridine ring may optionally be substituted, preferably at the 3- or 6-position, by a substituent selected from methoxy and hydroxy, a 2-indolinyl, 2-pyrrolidinyl, 2-pyrazinyl, 2-furyl, 2-thienyl or 3-quinolyl group, or a 4-imidazolylvinyl group; $R_{31}$ represents a 2(S)-carboxyindolinyl or 2-carboxy(2S,3aS,7aS)octahydro-indolyl group; and m is 2 or 3.

A more preferred group of the tripeptide derivatives of formula (I) provided by this invention are tripeptide derivatives represented by the following formula

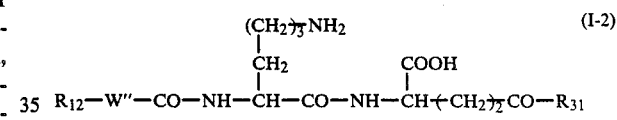

wherein $R_{12}$—W'''-represents a cyclobutyl, cyclopentyl, cyclobutyloxy or cyclopentyloxy group, a phenyl group which may optionally be substituted, at the 2- or 4-position, by a substituent selected from lower alkoxy (particularly methoxy) and hydroxy, a phenethyloxy group which may optionally be substituted by hydroxy at the 4-position of the benzene ring, or a pyridyl group which may optionally be substituted, preferably at the 2- or 6-position, by halogen (preferably, chlorine) or lower alkoxy; and $R_{31}$ represents a 2(S)-carboxyindolinyl or 2-carboxy(2S,3aS,7aS)octahydro-indolyl group, and salts thereof.

The tripeptide derivatives (I) of the invention have an amino group, and when $R_2$ and/or $R_4$ are hydrogen, a carboxyl group (or groups) as well. Hence, they form salts with various acids, for example inorganic acids such as hydrochloric acid and sulfuric acid, and organic acids such as trifluoroacetic acid and acetic acid, or can exist in the form of salts such as sodium, potassium, calcium and ammonium salts or basic amino acid salts. Pharmaceutically acceptable salts are preferred.

The tripeptide derivatives (I) of the invention can also exist in the form of hydrates or solvates such as a solvate with dioxane, and it should be understood that the tripeptide derivatives of this invention also include such hydrates and solvates.

The tripeptide derivatives (I) have at least two asymmetric carbon atoms, i.e. the carbon atom at the alpha-position of the basic amino acid moiety and the carbon atoms at the alpha-position of the glutamic acid moiety. Accordingly, the tripeptide derivatives (I) of this invention exist as a streoisomer or a steroisomeric mixture which are also included within this invention. Preferably, the configuration of the alpha-carbon of the basic amino acid moiety is L, and the alpha-carbon of the glutamic acid moiety is D. When the carbon atom to which —COOR$_4$ is bonded in R$_3$ is asymmetric, its configuration is preferably similar to that of L-type amino acid.

Typical examples of the tripeptide derivatives of formula (I) provided by this invention are given below.

1-[N$^2$-cyclobutylcarbonyl-L-lysyl-gamma-D-glutamyl]indoline-2(S)-carboxylic acid,
(2S,3aS,7aS)-1-[N$^2$-cyclobutylcarbonyl-L-lysylgamma-D-glutamyl]octahydro-1H-indole-2-carboxylic acid,
(2S,3aS,7aS)-1-[N$^2$-cycopentylcarbonyl-L-lysyl-gamma-D-glutamyl]octahydro-1H-indole-2-carboxylic acid,
1-[N$^2$-cyclohexylcarbonyl-L-lysyl-gamma-D-glutamyl]indoline-2(S)-carboxylic acid,
1-[N$^2$-cyclobutyloxycarbonyl-L-lysyl-gamma-D-glutamyl]indoline-2(S)-carboxylic acid,
(2S,3aS,7aS)-1-[N$^2$-cyclobutyloxycarbonyl-L-lysyl-gamma-D-glutamyl]octahydro-1H-indole-2-carboxylic acid,
(2S,3aS,7aS)-1-[N$^2$-cyclopentyloxycarbonyl-L-lysyl-gamma-D-glutamyl]octahydro-1H-indole-2-carboxylic acid,
1-[N$^2$-cyclopentyloxycarbonyl-L-lysyl-gamma-D-glutamyl]indoline-2(S)-carboxylic acid,
1-[N$^2$-cyclohexyloxycarbonyl-L-lysyl-gamma-D-glutamyl]indoline-2(S)-carboxylic acid,
(2S,3aS,7aS)-1-[N$^2$-cyclohexyloxycarbonyl-L-lysyl-gamma-D-glutamyl]octahydro-1H-indole-2-carboxylic acid,
1-[N$^2$-cyclohexylmethoxycarbonyl-L-lysyl-gamma-D-glutamyl]indoline-2(S)-carboxylic acid,
1-[N$^2$-cyclohexylethoxycarbonyl-L-lysyl-gamma-D-glutamyl]indoline-2(S)-carboxylic acid,
1-[N$^2$-benzoyl-L-lysyl-gamma-D-glutamyl]indoline-2(S)-carboxylic acid,
(2S,3aS,7aS)-1-[N$^2$-benzoyl-L-lysyl-gamma-D-glutamyl]octahydro-1H-indole-2-carboxylic acid,
(2S,3aS,7aS)-1-[N$^2$-(2-methoxybenzoyl)-L-lysyl-gamma-D-glutamyl]octahydro-1H-indole-2-carboxylic acid,
(2S,3aS,7aS)-1-[N$^2$-(4-chlorobenzoyl)-L-lysyl-gamma-D-glutamyl]octahydro-1H-indole-2-carboxylic acid,
(2S,3aS,7aS)-1-[N$^2$-(4-hydroxybenzoyl)-L-lysyl-gamma-D-glutamyl]octahydro-1H-indole-2-carboxylic acid,
(2S,3aS,7aS)-1-[N$^2$-(2-hydroxy-5-methoxybenzoyl)-L-lysyl-gamma-D-glutamyl]octahydro-1H-indole-2-carboxylic acid,
(2S,3aS,7aS)-1-[N$^2$-(2-hydroxy-5-bromobenzoyl)-L-lysyl-gamma-D-glutamyl]ocahydro-1H-indole-2-carboxylic acid,
1-[N$^2$-(benzyloxycarbonyl)-L-lysyl-gamma-D-glutamyl]-indoline-2(S)-carboxylic acid,
(2S,3aS,7aS)-1-[N$^2$-(benzyloxycarbonyl)-L-lysyl-gamma-D-glutamyl]octahydro-1H-indole-2-carboxylic acid,
1-[N$^2$-phenethyloxycarbonyl-L-lysyl-gamma-D-glutamyl]indoline-2(S)-carboxylic acid,
(2S,3aS,7aS)-1-[N$^2$-(phenethyloxycarbonyl)-L-lysyl-gamma-D-glutamyl[octahydro-1H-indole-2-carboxylic acid,
1-[N$^2$-(4-methoxyphenethyloxycarbonyl)-L-lysyl-gamma-D-glutamyl]indoline-2(S)-carboxylic acid,
1-[N$^2$-(3,4-methylenedioxybenzyloxycarbonyl)-L-lysyl-gamma-D-glutamyl]indoline-2(S)-carboxylic acid,
(2S,3aS,7aS)-1-[N$^2$-(4-hydroxyphenethyloxycarbonyl)-L-lysyl-gamma-D-glutamyl]octahydro-1H-indole-2-carboxylic acid,
1-[N$^2$-nicotinoyl-L-lysyl-gamma-D-glutamyl]indoline-2(S)-carboxylic acid,
(2S,3aS,7aS)-1-[N$^2$-nicotinoyl-L-lysyl-gamma-D-glutamyl]octahydro-1H-indole-2-carboxylic acid,
(2S,3aS,7aS)-1-[N$^2$-nicotinoyl-L-lysyl-gamma-D-glutamyl]octahydro-1H-indole-2-carboxylic acid monosodium salt,
(2S,3aS,7aS)-1-[N$^2$-isonicotinoyl-L-lysyl-gamma-D-glutamyl]octahydro-1H-indole-2-carboxylic acid,
(2S,3aS,7aS)-1-[N$^2$-(pyridine-2-carbonyl)-L-lysyl-gamma-D-glutamyl]octahydro-1H-indole-2-carboxylic acid,
(2S,3aS,7aS)-1-[N$^2$-(6-chloronicotinoyl)-L-lysyl-gamma-D-glutamyl]octahydro-1H-indole-2-carboxylic acid,
(2S,3aS,7aS)-1-[N$^2$-(6-methoxynicotinoyl)-L-lysyl-gamma-D-glutamyl]octahydro-1H-indole-2-carboxylic acid,
(2S,3aS,7aS)-1-[N$^2$-(6-ethoxynicotinoyl)-L-lysyl-gamma-D-glutamyl]octahydro-1H-indole-2-carboxylic acid,
(2S,3aS,7aS)-1-[N$^2$-(6-n-propyloxynicotinoyl)-L-lysyl-gamma-D-glutamyl]octahydro-1H-indole-2-carboxylic acid,
(2S,3aS,7aS)-1-[N$^2$-(6-isopropyloxynicotinoyl)-L-lysyl-gamma-D-glutamyl]octahydro-1H-indole-2-carboxylic acid,
(2S,3aS,7aS)-1-[N$^2$-(2-methylpyridin-5-yl)-L-lysyl-gamma-D-glutamyl]octahydro-1H-indole-2-carboxylic acid,
1-[N$^2$-(2-dimethylaminopyridin-5-yl)-L-lysyl-gamma-D-glutamyl]indoline-2(S)-carboxylic acid,
1-[N$^2$-(2-pyridineethoxycarbonyl)-L-lysyl-gamma-D-glutamyl]indoline-2(S)-carboxylic acid,
1-[N$^2$-((3-methoxypyridin-2-yl)methoxycarbonyl)-L-lysyl-gamma-D-glutamyl]indoline-2(S)-carboxylic acid,
1-[N$^2$-((3-hydroxypyridin-2-yl)methoxycarbonyl)-L-lysyl-gamma-D-glutamyl]indoline-2(S)-carboxylic acid,
(2S,3aS,7aS)-1-[N$^2$-(indoline-2(S)-carbonyl)-L-lysyl-gamma-D-glutamyl]octahydro-1H-indole-2-carboxylic acid,
1-[L-prolyl-L-lysyl-gamma-D-glutamyl]indoline-2(S)-carboxylic acid,
1-[D-prolyl-L-lysyl-gamma-D-glutamyl]indoline-2(S)-carboxylic acid,
1-[N$^2$-pyrazinoyl-L-lysyl-gamma-D-glutamyl]indoline-2(S)-carboxylic acid,
1-[N$^2$-(2-furoyl)-L-lysyl-gamma-D-glutamyl]indoline-2(S)-carboxylic acid,
(2S,3aS,7aS)-1-[N$^2$-(2-thiophenecarbonyl)-L-lysyl-gamma-D-glutamyl]octahydro-1H-indole-2-carboxylic acid,
(2S,3aS,7aS)-1-[N$^2$-(3-quinolinecarbonyl)-L-lysyl-gamma-D-glutamyl]octahydro-1H-indole-2-carboxylic acid,
1-[N$^2$-(4-imidazolylpropenoyl)-L-lysyl-gamma-D-glutamyl]indoline-2(S)-carboxylic acid,
(2S,3aS,7aS)-1-[N$^2$-(benzyloxycarbonyl)-L-ornithyl-gamma-D-glutamyl]octahydro-1H-indole-2-carboxylic acid, and (2S,3aS,7aS)-1-[N-(bensyloxycarbonyl)-S-(3-aminopropyl)-L-cysteinyl-gamma-D-glutamyl]octahydro-1H-indole-2-carboxylic acid sulfoxide.

The following compounds are especially preferred among the tripeptide derivatives of formula (I).

1-[$N^2$-cyclobutylcarbonyl-L-lysyl-gamma-D-glutamyl]indoline-2(S)-carboxylic acid, (2S,3aS,7aS)-1-[$N^2$-cyclobutylcarbonyl-L-lysyl-gamma-D-glutamyl]octahydro-1H-indole-2-carboxylic acid, (2S,3aS,7aS)-1-[$N^2$-cyclopentylcarbonyl-L-lysyl-gamma-D-glutamyl]octahydro-1H-indole-2-carboxylic acid, 1-[$N^2$-cyclobutyloxycarbonyl-L-lysyl-gamma-D-glutamyl]indoline-2(S)-carboxylic acid, (2S,3aS,7aS)-1-[$N^2$-cyclobutyloxycarbonyl-L-lysyl-gamma-D-glutamyl]octahydro-1H-indole-2-carboxylic acid, 1-[$N^2$-cyclopentyloxycarbonyl-L-lysyl-gamma-D-glutamyl]indoline-2(S)-carboxylic acid, (2S,3aS,7aS)-1-[$N^2$-cyclopentyloxycarbonyl-L-lysyl-gamma-D-glutamyl]octahydro-1H-indole-2-carboxylic acid, 1-[$N^2$-benzoyl-L-lysyl-gamma-D-glutamyl]indoline-2(S)-carboxylic acid, (2S,3aS,7aS)-1-[$N^2$-benzoyl-L-lysyl-gamma-D-glutamyl]octahydro-1H-indole-2-carboxylic acid, (2S,3aS,7aS)-1-[$N^2$-(2-methoxybenzoyl)-L-lysyl-gamma-D-glutamyl]octahydro-1H-indole-2-carboxylic acid, (2S,3aS,7aS)-1-[$N^2$-(4-hydroxybenzoyl)-L-lysyl-gamma-D-glutamyl]octahydro-1H-indole-2-carboxylic acid, 1-[$N^2$-phenethyloxycarbonyl)-L-lysyl-gamma-D-glutamyl]indoline-2(S)-caboxylic acid, (2S,3aS,7aS)-1-[$N^2$-(phenethyloxycarbonyl)-L-lysyl-gamma-D-glutamyl]octahydro-1H-indole-2-carboxylic acid, (2S,3aS,7aS)-1-[$N^2$-(4-hydroxyphenethyloxycarbonyl)-L-lysyl-gamma-D-glutamyl]octahydro-1H-indole-2-carboxylic acid, 1-[$N^2$-nicotinoyl-L-lysyl-gamma-D-glutamyl]indoline-2(S)-carboxylic acid, (2S,3aS,7aS)-1-[$N^2$-nicotinoyl-L-lysyl-gamma-D-glutamyl]octahydro-1H-indole-2-carboxylic acid, (2S,3aS,7aS)-1-[$N^2$-nicotinoyl-L-lysyl-gamma-D-glutamyl]octahydro-1H-indole-2-carboxylic acid monosodium salt, (2S,3aS,7aS)-1-[$N^2$-isonicotinoyl-L-lysyl-gamma-D-glutamyl]octahydro-1H-indole-2-carboxylic acid, (2S,3aS,7aS)-1-[$N^2$-(pyridine-2-carbonyl)-L-lysyl-gamma-D-glutamyl]octahydro-1H-indole-2-carboxylic acid, (2S,3aS,7aS)-1-[$N^2$-(6-chloronicotinoyl)-L-lysyl-gamma-D-glutamyl]octahydro-1H-indole-2-carboxylic acid, (2S,3as,7aS)-1-[$N^2$-(6-methoxynicotinoyl)-L-lysyl-gamma-D-glutamyl]octahydro-1H-indole-2-carboxylic acid, (2S,3aS,7aS)-1-[$N^2$-(6-ethoxynicotinoyl)-L-lysyl-gamma-D-glutamyl]octahydro-1H-indole-2-carboxylic acid, (2S,3aS,7aS)-1-[$N^2$-(6-n-propyloxynicotinoyl)-L-lysyl-gamma-D-glutamyl]octahydro-1H-indole-2-carboxylic acid, (2S,3aS,7aS)-1-[$N^2$-(6-isoprpyloxynicotinoyl)-L-lysyl-gamma-D-glutamyl]octahydro-1H-indole-2-carboxylic acid.

Preferred among the tripeptide derivative of formula (I-2) are those in which $R_{12}$—W'''- represents a phenyl group substituted by hydroxy or $C_{1-3}$ alkoxy at the 2- or 4-position, and $R_{31}$ represents 2(S)-carboxyindolinyl or 2-carboxy-(2S,3aS,7aS)octahydroindolyl. Those in which $R_{12}$—W'''- represents a 4-hydroxyphenyl are more preferred, and (2S,3aS,7aS)-1-[$N^2$-(4-hydroxybenzoyl)-L-lysyl-gamma-D-glutamyl]octahydro-1H-indole-2-carboxylic acid and (2S,3aS,7aS)-1-[$N^2$-nicotinoyl-L-lysyl-gamma-D-glutamyl)-octahydro-1H-indole-2-carboxylic acid are most preferred.

The tripeptide derivatives of formula (I) can be produced by (a) reacting a compound represented by the following formula

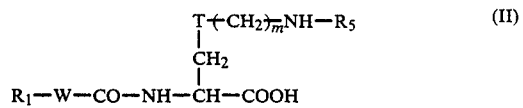

wherein $R_1$, W, T and m are as defined hereinabove and $R_5$ represents a hydrogen atom or an amino protecting group, or a reactive derivative at the carboxyl group, with a compound represented by the following formula

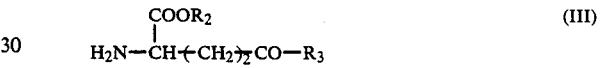

wherein $R_2$ and $R_3$ are the same as defined hereinabove, or an acid addition salt thereof, or (b) reacting a compound represented by the following formula

wherein $R_1$ and W are the same as defined hereinabove, or a reactive derivative thereof at the carboxyl group, with a compound represented by the following formula

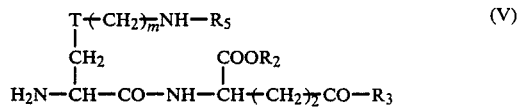

wherein $R_2$, $R_3$, $R_5$, T and m are the same as defined hereinabove, or an acid addition salt thereof, or (c) reacting a compound represented by the following formula

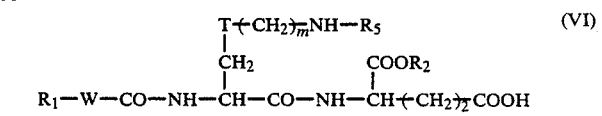

wherein $R_1$, $R_2$, $R_5$, T, W and m are the same as defined hereinabove, or a reactive derivative thereof at the carboxyl group or an intramolecular anhydride thereof, with a compound represented by the following formula

wherein R₃ is the same as defined above, or an acid addition salt thereof, and if required, removing the protective group which can exist from the resulting compound, and/or converting it into a salt.

The reactions utilized in the process variants (a), (b) and (c) are peptidization reactions, and can be carried out by conventional methods practiced in the synthesis of peptides [see, for example, Methoden der Organischen Chemie (edited by Houoen-Weyl), Vol. 15, Part I, Part II (1974)]. When the carboxylic acid compounds of formulae (II), (IV) and (VI) are reacted in free carboxylic acid form with the amine compounds of formulae (III), (V) and (VII), respectively, the reactions are conveniently carried out in the presence of a condensing agent such as N,N-dicyclohexylcarbodiimide, 1-ethyl-3-(3-dimethylaminopropyl)carbodiimide hydrochloride, carbonyl diimidazole, diphenylphosphoryl azide or diethyl cyanophosphate. When a carbodiimide is used as the condensing agent, 1-hydroxybenzotriazole, N-hydroxysuccinimide or N-hydroxy-5-norbornene-2,3-dicarboximide, for example, may optionally be added to the reaction system to inhibit racemization.

Instead of using such a condensing agent, the compounds of formulae (II), (IV) and (VI) may be reacted in the form of their reactive derivatives at the carboxyl group with the amine compounds of formulae (III), (V) and (VII). Examples of the reactive derivatives of the compounds of formulae (II), (IV) and (VI) are acid halides, acid azides, mixed acid anhydrides, active esters and active amides.

The reactions in the process variants (a), (b) and (c) are usually carried out in a solvent at a temperature of −40° to 40° C. An example of the solvent that can be used is tetrahydrofuran, dioxane, chloroform, methylene chloride, ethyl acetate, acetone, methyl ethyl ketone, dimethylformamide, acetonitrile, ethanol, methanol or water. Such a solvent may be used singly or in combination. When an acid occurs as a by-product or the compounds of formulae (III), (V) and (VII) are acid addition salts or the compounds of formulae (III), (V) and (VII) have a free carboxyl group, the reaction is preferably carried out in the presence of a base as an acid acceptor. An example of a base that can be used is an alkali hydroxide such as sodium hydroxide or potassium hydroxide, an alkali carbonate or bicarbonate such as sodium bicarbonate, sodium carbonate or potassium carbonate, or an organic base such as triethylamine, N-methylmorpholine, dicyclohexylamine, pyridine or 4-dimethylaminopyridine.

In the above reactions, starting compounds in which the amino group or the carboxyl group is protected may be used as is usually the case with peptide synthesis. All protective groups known in the field of peptide synthesis can be used to protect the amino or carboxyl group, but should preferably be selected according to the purpose (see Methoden der Organischen Chemie cited above). Benzyloxycarbonyl, tert-butoxycarbonyl and 3-nitro-2-pyridinesulfenyl may be cited as examples of the amino protecting group $R_5$. After the reaction, the protective groups may be removed in a customary manner. For example, lower alkyl esters and aralkyl esters as protective groups for the carboxyl group may be eliminated by hydrolysis using dilute alkalies, for example 1∼2N-NaOH or KOH. A benzyloxycarbonyl group or the benzyl group of a benzyl ester may be eliminated conveniently by catalytic reduction in the presence of palladium-carbon or palladium-carbon/ammonium formate or by the action of HBr/acetic acid. A tert-butoxycarbonyl group or the tert-butoxy group of a tert-butoxy ester may be eliminated by the action of a strong acid such as trifluoroacetic acid at room temperature or under ice cooling.

The tripeptide derivatives (I) of the invention produced as above may, as required, be converted to the above-exemplified salts in a customary manner.

The tripeptide derivatives (I) or salts thereof as produced above may be isolated and purified by a known method such as extraction, concentration, neutralization, filtration, recrystallization, column chromatography, high-performance liquid chromatography or an ion exchange resin in suitable combination.

The tripeptide derivatives (I) or salts thereof of this invention have excellent pharmacological activities, particularly antihypertensive activity and are useful as agents for preventing and treating cardiovascular diseases, such as hypertension and congestive heart failure.

The excellent antihypertensive activity of the tripeptide derivatives (I) or salts thereof of this invention can be demonstrated by the following in vivo antihypertensive activity test using renal hypertensive rats. The results of an in vitro ACE inhibiting activity test are also shown below.

Antihypertensive Activity

Male Sprague Dawley rats (5 weeks old) were subjected to constriction of the left renal artery with a silver clip (internal diameter: 0.22 mm) under light ether anesthesia. The right kidney and renal artery were left intact. About 6–10 weeks after clipping, rats showing a blood pressure above 180 mmHg were used. These treated rats are named two-kidney Goldblatt type renal hypertensive rats and considered as a typical model of reninangiotensin dependent hypertension.

The blood pressure was measured by a tail-cuff method using a programmed electro-sphygmomanometer (PE-300, Narco Biosystem, U. S. A.) after warming at 38° C. for 10 minutes in heating box.

The antihypertensive activity of test compounds was evaluated after single oral administration in renal hypertensive rats (3–5 rats/group). The results are shown in Table 1.

In Vitro ACE Inhibitory Activity

The assay medium contained an ACE preparation (rabbit lung), synthetic substrate (hippuryl-L-histidyl-L-leucine 5 mM), NaCl (300 mM) and phosphate buffer (100 mM, pH 8.3). It was mixed to a final volume of 0.300 ml and incubated at 37° C. for 30 minutes in the presence or absence of test compounds. After the reaction was terminated by adding 300 μl of 1N HCl, hippuric acid formed was extracted with 2 volume of ethyl acetate. After ethyl acetate was evaporated and distilled water was added, the hippuric acid was determined from its absorbance at 228 nm by spectrophotometer (Hitachi 100-41).

The degree of ACE inhibition was calculated from activities with and without test compounds. The $IC_{50}$ value (molar concentration required for the 50% inhibition of ACE activity) was obtained from a dose-inhibition curve. The results are shown in Table 1 below.

TABLE 1

$$R_1-W-CO-NH-CH(CH_2-T-(CH_2)_m-NH_2)-CO-NH-CH(COOR_2)-(CH_2)_2-CO-R_3$$

| Compound of Example | R₁—W— | T | m | R₂ | R₃ | Charge in blood pressure (mmHg) at 9 hours after administration*¹ | ACE inhibitory activity (IC₅₀; M) |
|---|---|---|---|---|---|---|---|
| 1 | C₆H₅—CH₂O— | single bond | 3 | H | indoline-2-COOH | −31 | $5.6 \times 10^{-9}$ |
| 3 | C₆H₅—(CH₂)₂O— | " | 3 | " | " | −36 | $1.3 \times 10^{-8}$ |
| 4 | cyclohexyl—O— | " | " | " | " | −28 | $8.4 \times 10^{-9}$ |
| 8 | 2-furyl— | " | " | " | " | −21 | $2.3 \times 10^{-8}$ |
| 9 | pyrrolidin-2-yl— | " | " | " | " | −21 | $3.6 \times 10^{-8}$ |
| 10 | (1H-imidazol-4-yl)—CH=CH— | single bond | 3 | H | indoline-2-COOH | −23 | $9.5 \times 10^{-8}$ |
| 11 | C₆H₅—CH₂O— | " | " | " | octahydroindoline-2-COOH | −37 | $3.5 \times 10^{-9}$ |
| 14 | " | " | 2 | " | " | −24 | $4.9 \times 10^{-9}$ |
| 15 | 3-pyridyl— | " | 3 | " | " | −45 | $6.4 \times 10^{-9}$ |
| 16 | cyclohexyl—CH₂O— | " | " | " | indoline-2-COOH | −21 | $1.3 \times 10^{-8}$ |
| 17 | pyrrolidin-2-yl—*D | " | " | " | " | −24 | $2.1 \times 10^{-8}$ |

TABLE 1-continued $$R_1-W-CO-NH-\underset{\underset{CH_2}{|}}{\overset{T(CH_2)_m NH_2}{C}H}-CO-NH-\underset{\underset{COOR_2}{|}}{C}H(CH_2)_2 CO-R_3$$

| Compound of Example | R₁—W— | T | m | R₂ | R₃ | Charge in blood pressure (mmHg) at 9 hours after administration[*1] | ACE inhibitory activity (IC₅₀; M) |
|---|---|---|---|---|---|---|---|
| 18 | cyclobutyl | single bond | 3 | H | octahydroindole-2-COOH | −42 | $7.5 \times 10^{-9}$ |
| 20 | 2-pyridyl | " | " | " | " | −37 | $6.8 \times 10^{-9}$ |
| 26 | Ph(CH₂)₂O— | " | " | " | " | −29 | $4.6 \times 10^{-9}$ |
| 27 | phenyl | " | " | " | " | −42 | $5.4 \times 10^{-9}$ |
| 28 | MeO-C₆H₄-(CH₂)₂O— | " | " | " | indoline-2-COOH | −29 | $1.1 \times 10^{-8}$ |
| 29 | 4-pyridyl | " | " | " | octahydroindole-2-COOH | −38 | $7.2 \times 10^{-9}$ |
| 30 | cyclopentyl-O— | single bond | 3 | H | octahydroindole-2-COOH | −38 | $5.8 \times 10^{-9}$ |
| 31 | cyclohexyl-O— | " | " | " | " | −23 | $5.0 \times 10^{-9}$ |
| 32 | cyclobutyl-O— | " | " | " | " | −26 | $4.6 \times 10^{-9}$ |
| 33 | " | " | " | " | indoline-2-COOH | −40 | $1.4 \times 10^{-8}$ |

TABLE 1-continued $$R_1-W-CO-NH-\underset{\underset{\underset{T+CH_2)_{\overline{m}}NH_2}{|}}{\overset{|}{CH_2}}}{CH}-CO-NH-\underset{\underset{COOR_2}{|}}{CH}(CH_2)_{\overline{2}}CO-R_3$$

| Compound of Example | $R_1-W-$ | T | m | $R_2$ | $R_3$ | Charge in blood pressure (mmHg) at 9 hours after administration*[1] | ACE inhibitory activity ($IC_{50}$; M) |
|---|---|---|---|---|---|---|---|
| 34 | 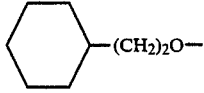 | " | " | " | " | −24 | $8.0 \times 10^{-9}$ |
| 35 | 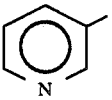 | " | " | " | " | −38 | $1.1 \times 10^{-8}$ |
| 36 |  | " | " | " | " | −23 | $2.2 \times 10^{-8}$ |
| 37 | 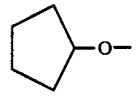 | single bond | 3 | H | 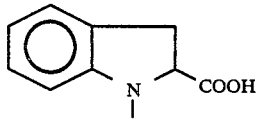 | −23 | $5.1 \times 10^{-9}$ |
| 38 | 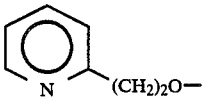 | " | " | " | " | −27 | $1.2 \times 10^{-8}$ |
| 39 |  | " | " | " | " | −27 | $1.1 \times 10^{-8}$ |
| 51 | 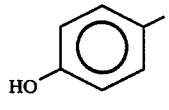 | " | " | " | 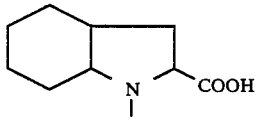 | −52 | $5.2 \times 10^{-9}$ |
| 52 | 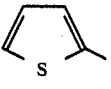 | " | " | " | " | −29 | $4.5 \times 10^{-9}$ |
| 53 |  | " | " | " | " | −27 | $4.6 \times 10^{-9}$ |
| 54 | 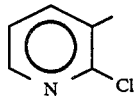 | single bond | 3 | H | 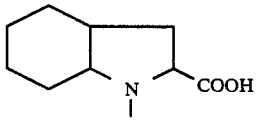 | −41 | $5.9 \times 10^{-9}$ |
| 55 | 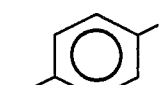 | " | " | " | " | −25 | $6.2 \times 10^{-9}$ |

TABLE 1-continued $$R_1-W-CO-NH-\underset{\underset{\underset{T+CH_2)_m NH_2}{|}}{CH_2}}{CH}-CO-NH-\underset{\underset{(CH_2)_2 CO-R_3}{|}}{CH}$$

with COOR$_2$ on the second CH

| Compound of Example | R$_1$—W— | T | m | R$_2$ | R$_3$ | Change in blood pressure (mmHg) at 9 hours after administration*1 | ACE inhibitory activity (IC$_{50}$; M) |
|---|---|---|---|---|---|---|---|
| 56 | 2-indolinyl (*S) | " | " | " | " | −22 | 8.2 × 10$^{-9}$ |
| 68 | pyrazinyl | " | " | " | indoline-2-COOH | −27 | 1.6 × 10$^{-8}$ |
| 69 | pyridyl | " | " | H (mono Na salt) | octahydroindoline-2-COOH | −44 | 7.8 × 10$^{-9}$ |
| 70 | o-methoxyphenyl | " | " | H | " | −38 | 5.4 × 10$^{-9}$ |
| 71 | cyclohexyl | single bond | 3 | H | indoline-2-COOH | −30 | 2.7 × 10$^{-8}$ |
| 74 | 3,4-methylenedioxybenzyloxy (—CH$_2$O—) | " | " | " | " | −32 | 6.6 × 10$^{-9}$ |
| 76 | benzyloxy (—CH$_2$O—) | \\S→O (dimethyl sulfoxide group) | " | " | octahydroindoline-2-COOH | −31 | 3.9 × 10$^{-9}$ |
| | 1-(L-lysyl-γ-D-glutamyl)indoline-2(S)—carboxylic acid*2 | | | | | −3*3 | 1.88 × 10$^{-8}$ |
| | 1-(N$^2$,N$^6$—dibenzyloxycarbonyl-L-lysyl-γ-D-glutamyl)indoline-2(S)—carboxylic acid*2 | | | | | −2*3 | 6.1 × 10$^{-9}$ |

*1 The values were obtained with oral administration in a dose of 10 mg/kg.
*2 The compounds disclosed in Journal of Medicinal Chemistry, 28(11), 1606-1611 (1985).
*3 The values were obtained with oral administration in a dose of 30 mg/kg. No antihypersensitive effect was seen not only at 9 hours but also at 1, 3, 5, 7 and 24 hours after oral administration.

Toxicity

Male STD-ddy strain mice weighing about 22 to 25 g were used. The oral LD$_{50}$ values of test compounds (Examples 15 and 51) in the mice were found to be more than 3,000 mg per kilogram of body weight. These results show that the toxicities of compounds are very weak.

The foregoing experimental results demonstrate that the tripeptide derivatives of formula (I) and the pharmaceutically acceptable salts thereof exhibit excellent antihypertensive activity with long duration and weak toxicity, and therefore, can be used as a medicament for treating hypertension and cardiovascular diseases such as congestive heart failure.

The route of administration of the tripeptide derivatives (I) of this invention may be oral, parenteral or intrarectal, but preferably, they are administered orally. The dosage of the tripeptide derivatives of formula (I)

or a pharmaceutically acceptable salt thereof varies depending upon the type of such an antihypertensively active compound, the method of administration, the condition, body weight, age, etc. of the patient. The dose is generally 0.001 to 5.0 mg per kilogram body weight per day, preferably 0.01 to 3.0 mg per kilogram body weight per day. Since the active tripeptide derivative (I) of the invention has a long-lasting effect, it is sufficient that the drug is taken once or twice a day in the total doses indicated.

Usually, the tripeptide derivative of formula (I) or its pharmaceutically acceptable salt is administered to a patient in the form of a pharmaceutical composition comprising a therapeutically effective and non-toxic amount of such a compound and a pharmaceutically acceptable carrier or diluent. The pharmaceutical composition is formulated by mixing the tripeptide derivative of formula (I) or its pharmaceutically acceptable salt with a pharmaceutically acceptable carrier or diluent. Suitable carriers or diluents are those which are customarily used in formulating pharmaceuticals and do not react with the tripeptide derivatives of formula (I) or the salts thereof. Specific examples of such carriers include lactose, starch, sucrose, microcrystalline cellulose, sodium carboxymethyl cellulose, calcium carboxymethyl cellulose, methylcellulose, gelatin, acacia, hydroxypropylcellulose, hydroxypropyl methylcellulose, polyvinylpyrrolidone, light anhydrous silicic acid, magnesium stearate, talc, titanium dioxide, sorbitan fatty acid esters, glycerides of saturated fatty acids, macrogol, propylene glycol, and water. The pharmaceutical composition may be in various dosage forms such as tablets, capsules, granules, fine granules, powders, syrups, suppositories, and injections which are formulated in a customary manner. Liquid preparations may be in such a form as to be dissolved or suspended in water or other suitable vehicles just prior to use. The tablets may be coated in known manner. If desired, the pharmaceutical composition may contain flavoring agents, aromatics, preservatives, buffers, salts for rendering the composition isotonic, etc.

Usually, the pharmaceutical composition may contain at least 0.5%, preferably 1 to 60%, of the tripeptide derivative of formula (I) or its pharmaceutically acceptable salt as an active ingredient. The composition may also contain other therapeutically effective compounds such as a diuretic agent, for example, hydrochlorothiazide, triamterene, spironolactone, furosemide, etc.

In the last-mentioned pharmaceutical composition, the amount of the diuretic agent used may, for example, be 25 to 50 mg of hydrochlorothiazide, 50 to 100 mg for triamterene, 50 to 100 mg for spironolactone and 10 to 160 mg for furosemide, each per 5 to 10 mg of the tripeptide derivative of formula (I). The same carriers or diluents as described above may be used in this composition, and the composition may be in any of the dosage forms described above.

The tripeptide derivative (I) and the uretic agent can be administered to a patient in each of the dosage forms described above.

The following Examples illustrate the present invention more specifically. It should be understood however that they do not limit the scope of the invention.

EXAMPLE 1

1-($N^2$-Benzyloxycarbonyl-L-lysyl-gamma-D-glutamyl)indoline-2(S)-carboxylic acid:

Ethyl 1-($O^1$-ethyl-gamma-D-glutamyl)indoline-2(S)-carboxylate (to rbe referred to as "diester A"; 1.5 g), 1.97 g of $N^2$-benzyloxycarbonyl-$N^6$-t-butoxycarbonyl-L-lysine and 0.99 g of 1-ethyl-3-(3-dimethylaminopropyl)carbodiimide hydrochloride (to be referred to as the "water-soluble carbodiimide hydrochloride) were reacted overnight at room temperature in methylene chloride with stirring. The reaction mixture was washed with 5% aquoeus sodium bicarbonate solution and 10% citric acid, dried over anhydrous sodium sulfate, and concentrated to dryness under reduced pressure. The residue was purified by silica gel column chromatography (eluent: chloroform). Recrystallization from n-hexane, followed by filtration, gave 2.7 g of ethyl 1-($N^2$-benzyloxycarbonyl-$N^6$-t-butoxycarbonyl-L-lysyl-$O^1$-ethyl-gamma-D-glutamyl)indoline-2(S)-carboxylate. An aliquot (2.3 g) of this product was dissolved in a mixture of dioxane and water, and 10 ml of 1NaOH was added. The mixture was stirred at room temperature for 1.5 hours. The reaction mixture was acidified with dilute hydrochloric acid, diluted with water, and then extracted with chloroform. The extract was dried over anhydrous sodium sulfate, and concentrated to dryness under reduced pressure. The residue was chromatographed on a column (2.5 cm in diameter and 40 cm in length) of CHP20P (a product of Mitsubishi Chemical Co., Ltd.; 75–100 microns) using acetonitrile/water (30%→50% gradient) as an eluent. Fractions containing the desired product were collected and concentrated to dryness under reduced pressure. The residue was crystallized from ether/n-hexane and collected by filtration to give 1.6 g of 1-($N^2$-benzyloxycarbonyl-$N^6$-t-butoxycabonyl-L-lysyl-gamma-D-glutamyl)indoline-2(S)-carboxylic acid having a melting point of 121° to 129° C. (decomp.).

Trifluoroacetic acid (20 ml) was added to 1.1 g of this product under ice cooling, and the mixture was stirred for 15 minutes and then concentrated to dryness under reduced pressure at room temperature. The residue was purified by column chromatography (CHP20P column; 0%→60% acetonitrile/water gradient). The desired fractions were concentrated under reduced pressure, and the concentration was stopped when the crystals began to precipitate. The residue was cooled and the precipitated crystals were collected by filtration to obtain 0.68 g of the captioned compound.

Melting point: 190°–204° C. (decomp.)

$[\alpha]_D^{27}$: −78.5° (1N-NaOH)

Elemental analysis for $C_{28}H_{34}N_4O_8 \cdot 1.25H_2O$: Calculated (%): C: 58.27, H: 6.38, N: 9.71. Found (%): C: 58.51, H: 6.48, N: 9.92.

EXAMPLES 2–7

In the same manner as in Example 1, the following compounds wre synthesized.

1-($N^2$-Benzyloxycarbonyl-L-ornithinyl)-gamma-D-glutamyl)indoline-2(S)-carboxylic acid (Example 2):

Melting point: 204°–211° C. (decomp.)

$[\alpha]_D^{27}$: −79.0° (1N-NaOH)

Elemental analysis for $C_{27}H_{32}N_4O_8 \cdot 1.25H_2O$: Calculated (%): C: 57.59, H: 6.18, N: 9.95. Found (%): C: 57.58, H: 6.10, N: 9.81.

1-(N$^2$-Phenethyloxycarbonyl-L-lysyl-gamma-D-glutamyl)indoline-2(S)-carboxylic acid (Example 3):
Melting point: 199°–204° C.
$[\alpha]_D^{26}$: −82.1° (1N-NaOH)
Elemental analysis for C$_{29}$H$_{36}$N$_4$O$_8$.1.5H$_2$O: Calculated (%): C: 58.48, H: 6.60, N: 9.41. Found (%): C: 58.25, H: 6.82, N: 9.31.

1-(N$^2$-Cyclohexyloxycarbonyl-L-lysyl-gamma-D-glutamyl)indoline-2(S)-carboxylic acid (Example 4):
Melting point: 197°–205° C.
$[\alpha]_D^{27}$: −85.3° (1N-NaOH)
Elemental analysis for C$_{27}$H$_{38}$N$_4$O$_8$.1.75H$_2$O: Calculated (%): C: 56.09, H: 7.24, N: 9.69. Found (%): C: 56.15, H: 7.59, N: 9.84.

1-(N$^2$-Methoxycarbonyl-L-lysyl-gamma-D-glutamyl)indoline-2(S)-carboxylic acid (Example 5):
$[\alpha]_D^{28}$: −86.8° (1N-NaOH)
Elemental analysis for C$_{29}$H$_{36}$N$_4$O$_9$.2H$_2$O: Calculated (%): C: 51.36, H: 6.43, N: 10.90. Found (%): C: 51.36, H: 6.66, N: 10.89.

1-(N$^2$-n-Octyloxycarbonyl-L-lysyl-gamma-D-glutamyl)indoline-2(S)-carboxylic acid (Example 6):
Melting point: 199°–202° C.
$[\alpha]_D^{28}$: −82.3° (1N-NaOH)
Elemental analysis for C$_{29}$H$_{44}$N$_4$O$_8$.2.5H$_2$O: Calculated (%): C: 56.02, H: 7.94, N: 9.01. Found (%): C: 56.29, H: 7.98, N: 9.13.

1-(N$^2$-Cycloheptyloxycarbonyl-L-lysyl-gamma-D-glutamyl)indoline-2(S)-carboxylic acid (Example 7):
Melting point: 190°–195° C.
$[\alpha]_D^{25}$: −84.6° (1N-NaOH)
Elemental analysis for C$_{28}$H$_{40}$N$_4$O$_8$.1.75H$_2$O: Calculated (%): C: 56.79, H: 7.40, N: 9.46. Found (%): C: 56.68, H: 7.46, N: 9.39.

EXAMPLE 8

1-[N$^2$-(2-Furoyl)-L-lysyl-gamma-D-glutamyl]indoline-2(S)-carboxylic acid

2-Furanecarboxylic acid (2.0 g), 2.26 g of N-hydroxysuccinimide and 3.76 g of the water-soluble carbodiimide hydrochloride were stirred overnight at room temperature in tetrahydrofuran (THF for short)/methylene chloride. The reaction mixture was concentrated to dryness under reduced pressure, and the residue was extracted with ethyl acetate. The organic layer was washed successively with 10% hydrochloric acid, saturated aqueous sodium bicarbonate solution and saturated aqueous sodium chloride solution, dried over anhydrous sodium sulfate, and concentrated to dryness under reduced pressure. The residue was recrystallized from isopropanol to give 2.8 g of N-(2-furoyloxy)succinimide (melting point 126°–127° C.). To a solution of 1.79 g of the resulting succinimide and 2.0 g of N$^6$-benzyloxycarbonyl-L-lysine in THF/water was added 2.9 g of triethylamine, and the mixture was stirred overnight at room temperature. THF was evaporated under reduced pressure, and the residual solution was adjusted to pH 2–3 with 10% hydrochloric acid, and then extracted with ethyl acetate. The extract was dried over anhydrous sodium sulfate, and concentrated to dryness under reduced pressure. The residue was purified by column chromatography (CHP20P column; 30%→60% acetonitrile/water gradient) to give 2.3 g of N$^2$-(2-furoyl)-N$^6$-benzyloxycarbonyl-L-lysine $[\alpha]_D^{25}$: −4.6° (methanol). An aliquote (1.35 g) of this product and 1.0 g of the diester A were dissolved in methylene chloride, and 0.66 g of the water-soluble carbodiimide hydrochloride was added. The mixture was stirred overnight at room temperature. The reaction mixture was washed successively with 10% hydrochloric acid, saturated aqueous sodium bicarbonate solution and water, dried over anhydrous sodium sulfate, and concentrated to dryness under reduced pressure. The residue was reprecipitated from ether/ethanol to give 1.8 g of ethyl 1-[N$^2$-(2-furoyl)-N$^6$-benzyloxycarbonyl-L-lysyl-O$^1$-ethyl-gamma-D-glutamyl]indoline-2(S)-carboxylate (mp: 120°–123° C.). To a solution of 1.65 g of the resulting ethyl ester in dioxane was added 6.85 ml of 1N-NaOH, and the mixture was stirred at room temperature for 1 hour. The mixture was then acidified with 10% hydrochloric acid, and then extracted with ethyl acetate. The organic layer was washed with saturated aqueous sodium chloride solution, dried over anhydrous sodium sulfate, and concentrated under reduced pressure. The residue was crystallized from petroleum ether/ethyl acetate, and collected by filtration to give 1.50 g of 1-[N$^2$-(2-furoyl)-N$^6$-benzyloxycarbonyl-L-lysyl-gamma-D-glutamyl]indoline-2(S)-carboxylic acid. To a methanol solution of 1.35 g of this product were added 0.35 g of ammonium formate and 0.4 g of 10% palladium carbon, and the mixture was stirred at room temperature for 7 hours. The catalyst was removed, and methanol was evaporated under reduced pressure. Ethyl acetate was then added, and the mixture was extracted with 10% hydrochloric acid. The extract was chromatographed on a column of CHP20P using acetonitrile/water (0%→60% gradient) as an eluent to give a fraction containing about 70% of the desired product. The fraction was purified by column chromatography [a column of ODS-Q3 (a product of Wako Pure Chemical Co., Ltd.) having a diameter of 4 cm and a length of 30 cm; acetonitrile/1% trifluoroacetic acid=1/9)] to give 0.65 g of a powder. The powder was further chromatographed on a column of CHP20P (0%→60% acetonitrile/water gradient), and concentrated to dryness under reduced pressure. The residue was dissolved in water, and lyophilized to give 0.3 g of the captioned compound.

$[\alpha]_D^{25}$: −67.1° (1N-NaOH)
Elemental analysis for C$_{25}$H$_{30}$N$_4$O$_8$.2.25H$_2$O: Calculated (%): C: 54.10 H: 6.27, N: 10.09. Found (%): C: 54.16, H: 6.17, N: 9.98.

EXAMPLE 9

In the same way as in Example 8, 1-(L-prolyl-L-lysyl-gamma-D-glutamyl)indoline-2(S)-carboxylic acid was produced.

$[\alpha]_D^{26}$: −99.1° (1N-NaOH)
Elemental analysis for C$_{25}$H$_{35}$N$_5$O$_7$.3.5H$_2$O: Calculated (%): C0 51.71, H: 7.29, N: 12.06. Found (%): C: 51.48, H: 7.31, N: 12.02.

EXAMPLE 10

1-{N$^2$-[3-(4-Imidazolyl)-propenoyl]-L-lysyl-gamma-D-glutamyl}indoline-2(S)-carboxylic acid:

Ammonium formate (0.56 g) and 0.4 g of 10% palladium carbon were added to an ethanol solution of 2.1 g of ethyl 1-(N$^2$-benzyloxycarbonyl-N$^6$-t-butoxycarbonyl-L-lysyl-O$^1$-ethyl-gamma-D-glutamyl)indoline-2(S)-carboxylate (see Example 1), and the mixture was stirred at room temperature for 1 hour. The catalyst was removed by filtration, and the mother liquor was concentrated under reduced pressure. Ethyl acetate was added to the residue, and the mixture was washed with saturated aqueous sodium bicarbonate solution annd saturated aqueous sodium chloride solution and then dried over anhydrous sodium sulfate to give 1.7 g of ethyl 1-($N^6$-t-butoxycarbonyl-L-lysyl-$O^1$-ethyl-gamma-D-glutamyl)indoline-2(S)-carboxylate (mp.: 114°–117° C.). To a solution of 1.4 g of the product and 0.4 g of urocanic acid in dimethylformamide (DMF for short)/methylene chloride was added 1.17 g of the water-soluble carbodiimide hydrochloride, and the mixture was stirred overnight at room temperature. The solvent was evaporated under reduced pressure. The residue was crystallized in saturated aqueous sodium bicarbonate solution, and collected by filtration. The crystals were washed with water, and reprecipitated from ether/ethanol to give 1.4 g of a powder. It was purified by silica gel column chromatography (methanol/chloroform=1/9) to give 1.0 g of a powder. An aliquot (0.9 g) of the resulting powder was dissolved in 20 ml of dioxane, and 3.8 ml of 1N-NaOH was added. The mixture was stirred at room temperature for 3 hours, neutralized with aqueous potassium hydrogensulfate solution, and concentrated under reduced pressure. The residue was dissolved in water. The solution was adjusted to pH 5 with aqueous potassium hydrogensulfate solution, and chromatographed on a column of CHP20P (0%→60% acetonitrile/water gradient) to give 0.65 g of a powder. An aliquot (0.55 g) of this powder was left to stand together with 20 ml of trifluoroacetic acid under ice cooling for 30 minutes, and then trifluoroacetic acid was evaporated under reduced pressure at room temperature. The residue was chromatographed on a column of CHP20P (0%→30% acetonitrile/water gradient), and the resulting purified fractions were concentrated. The residue was lyophilized to give 0.33 g of the captioned compound.

$[\alpha]_D^{25}$: −43.1° (1N-NaOH)

Elemental analysis for $C_{26}H_{32}N_6O_7.3H_2O$: Calculated (%): C: 52.52, H: 6.44, N: 14.13 Found (%): C: 52.38, H: 6.50, N: 14.14

EXAMPLE 11

(2S,3aS,7aS)-1-($N^2$-Benzyloxycarboxyl-L-lysyl-gamma-D-glutamyl)octahydro-1H-indole-2-carboxylic acid The water-soluble carbodiimide hydrochloride (15.8 g) was added to a methylene chloride solution containing 24.5 g of N-benzyloxycarbonyl-$O^1$-ethyl-D-glutamic acid, 17.5 g of ethyl (2S,3aS,7aS)octahydro-1H-indole-2-carboxylate hydrochloride and 7.58 g of triethylamine, and the mixture was stirred overnight at room temperature. The reaction mixture was successively washed with saturated aqueous sodium bicarbonate solution, water, 10% hydrochloric acid and water, dried over anhydrous sodium sulfate, and concentrated to dryness under reduced pressure to give 34.1 g of an oily substance. The oily substance was dissolved in 400 ml of ethanol, and 3 g of 10% palladium carbon was added. While the mixture was stirred at room temperature, 12 g of ammonium formate was added in three divided portions. After 1 hour, the catalyst was removed by filtration, and the filtrate was acidified with hydrohcloric acid and concentrated to dryness under reduced pressure. The residue was dissolved in water, and washed with ethyl acetate. The aqueous layer was alkalified with sodium bicarbonate, and extracted with methylene chloride. The organic layer was dried over anhydrous sodium sulfate, and concentrated to dryness under reduced pressure to give 23.5 g of ethyl (2S,3aS,7aS)-1-($O^1$-ethyl-gamma-D-glutamyl)octahydro-1H-indole-2-carboxylate (to be referred to as the "diester B") as an oily substance. An aliquot (23 g) of the diester B was dissolved in 150 ml of ethanol, and 210 ml of 1N-NaOH was added. The mixture was stirred at room temperature for 5.5 hours, acidified with hydrochloric acid, and concentrated under reduced pressure. The residual solution was purified by column chromatography (a column of CHP20P; 0%→30% acetonitrile/water gradient). The purified fractions were concentrated to dryness under reduced pressure to give 6.31 g of a product. The insufficiently purified fractions were concentrated to dryness under reduced pressure. The residue was dissolved in water, neutralized with sodium bicarbonate and again purified by column chromatography (a column of CHP20P; 0%→30% acetonitrile/water gradient) to obtain 8.70 g of a product. These products were combined to give 15.01 g of (2S,3aS,7aS)-1-(gamma-D-glutamyl)octahydro-1H-indole-2-carboxylic acid (mp. 191°–192° C.) To an aqueous solution of 2 g of the resulting product and 2.68 ml of triethylamine was added 40 ml of THF. With stirring, 3.06 g of $N^2$-benzyloxycarbonyl-$N^6$-t-butoxycarbonyl-L-lysine N-hydroxysuccinimide ester was added. The mixture was stirred overnight at room temperature, and then concentrated under reduced pressure. The residual solution was mixed with 10% of citric acid, and extracted with ethyl acetate. The organic layer was washed with saturated sodium chloride solution, dried over anhydrous sodium sulfate, and concentrated under reduced pressure to give 3.96 g of a powder. An aliquot (3.46 g) of this powder was left to stand in 35 ml of trifluoroacetic acid for 20 minutes under ice cooling, and then concentrated to dryness under reduced pressure. The residue was dissolved in water, adjusted to pH 4 with sodium bicarbonate, and purified by column chromatography (a column of CHP20P; 0%→60% acetonitrile/water gradient). The desired fractions were concentrated to dryness under reduced pressure to give 1.6 g of the captioned compound as a white powder.

$[\alpha]_D^{26}$: −40.0° (1N-NaOH)

Elemental analysis for $C_{28}H_{40}N_4O_8.1.71H_2O$: Calculated (%): C, 56.79, H: 7.40, N: 9.46. Found: (%): C: 56.88, H: 7.47, N: 9.33.

EXAMPLE 12

In the same way as in Example 11, N-($N^2$-benzyloxycarbonyl-L-lysyl-gamma-D-glutamyl)-N-(4-methoxyphenyl)alanine was produced.

$[\alpha]_D^{28}$: −12.0° (1N-NaOH)

Elemental analysis for $C_{29}H_{38}N_4O_9.1H_2O$: Calculated (%): C: 57.61, H: 6.67, N: 9.27. Found (%): C: 57.33, H: 6.74, N: 9.24.

EXAMPLE 13

Ethyl (2S,3aS,7aS)-1-($N^2$-Benzyloxycarbonyl-L-ornithinyl-gamma-D-glutamyl)octahydro-1H-indole-2-carboxylate In 20 ml of methylene chloride were dissolved 1.81 g of $N^2$-benzyloxycarbonyl-$N^5$-t-butoxycarbonyl-L-ornithine and 1.75 g of the diester B, and 1.04 g of the water-soluble carbodiimide hydrochloride was added to the solution. The mixture was stirred overnight at room temperature. The reaction mixture was washed successively with 10% citric acid, water, saturated aqueous sodium bicarbonate solution, and water, dried over anhydrous sodium sulfate, and concentrated to dryness under reduced pressure to give 3.2 g of a viscous oily substance. An aliquot (3.0 g) of the oily substance was dissolved in 20 ml of trifluoroacetic acid, and with ice cooling, left to stand for 15 minutes. Trifluoroacetic acid was evaporated under reduced pressure. The residue was mixed with aqueous sodium bicarbonate solution, and extracted with ethyl acetate. The organic layer was extracted with 10% hydrochloric acid. The aqueous layer was alkalified with sodium bicarbonate and extracted with ethyl acetate. The organic layer was dried over anhydrous sodium sulfate and concentrated to dryness under reduced pressure to give 1.2 g of a viscous oily substance. The oily substance was dissolved in ethanol, and 3 ml of 1N-NaOH was added. The mixture was stirred for 30 minutes under ice cooling. The solution was mixed with 3 ml of 1N hydrochloric acid and concentrated under reduced pressure. The residue was purified by column chromatography (a column of CHP20P; 0%→60% acetonirile/water gradient). The purified fractions were concentrated to dryness under reduced pressure. The residue was lyophilized to give 0.60 g of the captioned compound as a white powder.

$[\alpha]_D^{25}$: $-46.0°$ (ethanol)

Elemental analysis for $C_{29}H_{42}N_4O_8 \cdot 1.5H_2O$: Calculated (%): C: 57.89, H: 7.54, N: 9.31. Found (%): C: 57.74, H: 7.33, N: 9.29.

EXAMPLE 14

(2S,3aS,7aS)-1-(N²-Benzyloxycarbonyl-L-ornithinyl-gamma-D-glutamyl)octahydro-1H-indole-2-carboxylic acid The final compound (0.5 g) produced in Example 13 was dissolved in ethanol, and 5 ml of 1N-NaOH was added. The mixture was stirred at room temperature for 3 hours, and 5 ml of 1N hydrochloric acid was added. The mixture was then concentrated under reduced pressure, and the residue was chromatographed on a column of CHP20P (0%→60% acetonitrile/water gradient). The purified fractions were concentrated to dryness under reduced pressure. The residue was lyophilized to give 0.30 g of the captioned compound as a white powder.

$[\alpha]_D^{26}$: $-39.4°$ (1N-NaOH)

Elemental analysis for $C_{27}H_{38}N_4O_8 \cdot 2H_2O$: Calculated (%): C: 55.66, H: 7.27, N: 9.62. Found (%) C: 55.39, H: 7.08, N: 9.49.

EXAMPLE 15

(2S,3aS,7aS)-1-(N²-Nicotinoyl-L-lysyl-gamma-D-glutamyl)octahydro-1H-indole-2-carboxylic acid

Method (a)

To a mixture of 20 ml of THF and 3 ml of water were added 4.42 g of N⁶-benzyloxycarbonyl-N²-t-butoxycarbonyl-L-lysine N-hydroxysuccinimide ester, 2.89 g of (2S,3aS,7aS)-1-(gamman-D-glutamyl)octahydro-1H-indole-2-carboxylic acid (see Example 11) and 2.6 ml of triethylamine, and the mixture was stirred for 5 hours at room temperature. The reaction mixture was concentrated under reduced pressure. The residue was mixed with aqueous saturated sodium chloride solution and washed with ethyl acetate. The aqueous layer was acidified with 10% citric acid, and extracted with ethyl acetate. The organic layer was washed with saturated sodium chloride solution, dried over anhydrous sodium sulfate, and concentrated to dryness under reduced pressure to give 5.19 g of a residue. The residue was purified by column chromatography (a column of CHP20P; 0%→60% acetonitrile/water gradient). The resulting fractions were concentrated to dryness under reduced pressure. The residue was dissolved in dioxane/water, and lyophilized to give 4.7 g of (2S,3aS,7aS)-1-(N⁶-benzyloxycarbonyl-N²-t-butoxycarbonyl-L-lysyl-gamma-D-glutamyl)octahydro-1H-indole-2-carboxylic acid. An aliquot (2.27 g) of the product was dissolved in 50 ml of trifluoroacetic acid, and left to stand for 15 minutes under ice cooling, and thereafter concentrated to dryness under reduced pressure. The residue was dissolved in water, adjusted to pH 4, and chromatographed on a column of CHP20P (0%→50% acetonitrile/water gradient). The desired fractions were concentrated under reduced pressure to give 1.15 g of (2S,3aS,7aS)-1-(N⁶-benzyloxycarbonyl-L-lysyl-gamma-D-glutamyl)octahydro-1H-indole-2-carboxylic acid as a glassy substance. An aliquot (1.0 g) of this glassy substance was dissolved in a mixture of N,N-dimethylformamide and tetrahydrofuran, and 0.5 ml of triethylamine and 0.39 g of N-(nicotinoyloxy)succinimide were added, and the mixture was stirred overnight at room temperature. Dilute hydrochloric acid was added to the reaction mixture, and the mixture was extracted with ethyl acetate. The extract was dried over anhydrous sodium sulfate, and concentrated to dryness under reduced pressure. The resulting glassy substance was dissolved in 25 ml of ethanol, and 0.6 g of ammonium formate and 0.3 g of 10% palladium carbon were added. The mixture was stirred at room temperature for 3 hours. The catalyst was removed by filtration, and the mother liquor was concentrated to dryness under reduced pressure. The reidue was chromatographed on a column of CHP20P (0%→60% acetonitrile/water gradient). The desired fractions were concentrated to dryness under reduced pressure. The residue was lyophilizded to give 0.5 g of the captioned compound.

$[\alpha]_D^{28}$: $-27.2°$ ($H_2O$)

Elemental analysis for $C_{26}H_{37}N_5O_7 \cdot 2.25H_2O$: Calculated (%): C: 54.58, H: 7.31, N: 12.24. Found (%) C: 54.62, H: 7.25, N: 12.20.

Method (b)

D-glutamic acid (18 g) and 31.75 g of sodium carbonate were dissolved in 200 ml of water, and then 37.5 g of N-carboethoxyphthalamide was added under ice cooling. The mixture was then stirred at room temperature for 4 hours. The insoluble materials were removed by filtration. The solution was acidified with 6N hydrochloric acid, and left to stand overnight at 4° C. The precipitated crystals were collected by filtration, washed with cold water, and dried to give 33.2 g of N-phthaloyl-D-glutamic acid (mp. 162°-164° C.). An aliquot (30 g) of this compound was added to 90 ml of acetic anhydride, and the mixture was stirred at 55° C. until it dissolved. Immediately after dissolving, the soluton was cooled, and 150 ml of anhydrous ether/n-hexane (2:1) was added. The precipitated crystals were collected by filtration to give 18.2 g of N-phthaloyl-D-glutamic anhydride (mp. 203°-206° C.). (2S,3aS,7aS)octahydro-1H-indole-2-carboxylic acid (6.13 g) was dissolved in 40 ml of pyridine, and 9.39 g of N-phthaloyl-D-glutamic anhydride was added. The mixture was stirred at room temperature for 2 hours. Ethyl acetate was added to the reaction mixture, and the mixture was washed successively with dilute hydrochloric acid and aqueous sodium chloride solution, and dried. The solvent was evaporated, and the residue was crystallized from a small amount of ethyl acetate. The crystals were collected by filtration, washed with ether and dried to give 13.1 g of (2S,3aS,7aS)-1-(N-phthaloyl-gamma-D-glutamyl)octahydro-1H-indole-2-carboxylic acid (mp. 194°-198° C.). The resulting compound was dissolved in 200 ml of ethanol, and 6.13 g of hydrazine monohydrate was added. The mixture was stirred overnight at room temperature, and 60 ml of water was added. The solution was adjusted to pH 4-5 with 12N hydrochloric acid, and the precipitate was removed by filtration. The mother liquor was concentrated. The residue was chromatographed on a column of HP-20 (a product of Mitsubishi Chemical Co., Ltd.). The column was washed with water and eluted with 70% methanol. Fractions containing the desired product were concentrated under reduced pressure to give 6.13 g of (2S,3aS,7aS)-1-(gamma-D-glutamyl)octahydro-1H-indole-2-carboxylic acid (mp. 191°-192° C.). An aliquot (1.8 g) of this compound and 1.28 g of sodium carbonate were dissolved in a mixture of 40 ml of acetonitrile and 30 ml of water. The solution was cooled to $-10°$ C., and with stirring, 2.1 g of $N^6$-benzyloxycarbonyl-L-lysine N-carboxylic anhydride was added. The mixture was stirred at $-10°$ C. for 2 hours. The reaction mixture separated into two layers. The aqueous layer was washed with cold acetonitrile, and 200 ml of ethanol was added. The precipitate was removed by filtration. The mother liquor was concentrated, and chromatographed on a column of DHP20P (0%→60% acetonitrile/water gradient). Fractions containing the desired product were concentrated to dryness under reduced pressure to give 1.9 of (2S,3aS,7aS)-($N^6$-benzyloxycarbonyl-L-lysyl-gamma-D-glutamyl)octahydro-1H-indole-2-carboxylic acid. This product was dissolved in 30 ml of ethanol, and 0.9 g of ammonium formate and 0.5 g of 10% palladium carbon were added. The mixture was stirred overnight at room temperature. The catalyst was removed by filtration, and the mother liquor was concentrated to dryness under reduced pressure. The residue was chromatographed on a column of CHP20P (0%→30% acetonitrile/water gradient). Fractions containing the desired product were concentrated to dryness under reduced prressure. The residue was lyophilized to give 1.05 g of (2S,3aS,7aS)-1-(L-lysyl-gamma-D-glutamyl)octahydro-1H-indole-2-carboxylic acid $\{[\alpha]_D^{30}: -5.4°$ (H$_2$O)$\}$. An aliquot (1.0 g) of the resulting carboxylic acid and 0.46 g of sodium carbonate were dissolved in a mixture of 10 ml of THF and 30 ml of water, and with vigorous stirring under ice cooling, 0.39 g of nicotinoyl chloride hydrochloride was added. The mixture was further stirred for 2 hours. The reaction mixture was concentrated under reduced pressure, and adjusted to pH 2-3 with dilute hydrochloric acid. The solution was chromatographed on a column of CHP20P (0%→60% acetonitrile/water gradient). Fractions containing the desired product were concentrated to dryness under reduced pressure and lyophilized to give 0.15 g of the captioned compound.

Method (c)

A mixture of 5.0 g of D-glutamic acid and 7.1 g of sodium carbonate was dissolved in a mixture of 170 ml of water and 200 ml of acetonitrile, and a solution of 11 g of $N^6$-benzyloxycarbonyl-L-lysine $N^2$-carboxylic anhydride in acetonitrile was added at $-10°$ C. with stirring. The mixture was stirred further for 2 hours at $-10°$ C. The aqueous layer was washed with cold acetonitrile, neutralized, and concentrated under reduced pressure. The residue was purified by CHP20P column chromatograph (0%→50% acetonitrile/water gradient), and recrystallized from dilute alcohol to give 6.3 g of $N^6$-benzyloxycarbonyl-L-lysyl-D-glutamic acid (mp. 149°-150° C.). An aliquot (6.0 g) of this product and 3.0 g of sodium carbonate were dissolved in a mixture of 100 ml of water and 40 ml of THF, and with stirring under ice cooling, a THF solution of 3.2 g of N-(nicotinoyloxy)succinimide was added. The mixture was stirred at room temperature for 2 hours. The reaction mixture was neutralized and concentrated under reduced pressure. The residual solution was adjusted to pH 2 and subjected to CHP20P column chromatography (0%→60% acetonitrile/water gradient). Fractions containing the desired product were concentrated to dryness under reduced pressure to give 4.8 g of $N^2$-nicotinoyl-$N^6$-benzyloxycarbonyl-L-lysyl-D-glutamic acid. An aliquot (4.0 g) of this product was stirred in acetic anhydride (100 ml) for 2 hours and concentrated to dryness under reduced pressure at a low temperature, and the residue was dissolved in 50 ml of methylene chloride. The solution was washed with water and dried, and the solvent was evaporated to give 3.5 g of roughly purified $N^2$-nicotinoyl-$N^6$-benzyloxycarbonyl-L-lysyl-D-glutamic anhydride. The resulting anhydride (3.5 g) was added to a solution of 1.2 g of (2S,3aS,7aS-)octahydro-1H-indole-2-carboxylic acid in 15 ml of pyridine, and the mixture was stirred at room temperature for 2 hours. The reaction mixture was concentrated to dryness under reduced pressure at room temperature. The residue was dissolved in water, and the pH of the solution was adjusted to 2. The solution was subjected to CHP20P column chromatography (0%→60% acetonitrile/water gradient). Fractions containing the desired product were concentrated to dryness under reduced pressure to give 1.3 g of (2S,3aS,7aS)-1-($N^2$-nicotinoyl-$N^6$-benzyloxycarbonyl-L-lysyl-gamma-D-glutamyl)octahydro-1H-indole-2-carboxylic acid. This compound was dissolved in 25 ml of ethanol, and 1.2 of ammonium formate and 0.5 g of 10% palladium carbon were added. The mixture was stirred at room temperature for 3 hours. The catalyst was removed by filtration, and the mother liquor was concentrated to dryness under reduced pressure. The residue was purified by CHP20P column chromatography (0%→60% acetonitrile/water gradient), and lyophilized to give 0.8 g of the same final product as obtained in method (a) above.

EXAMPLES 16-22

The following compounds were synthesized in the same way as in Example 15 [method (a)].

1-($N^2$-Cyclohexylmethoxycarbonyl-L-lysyl-gamma-D-glutamyl)indoline-2(S)-carboxylic acid (Example 16):
Melting point: 186°-191° C.
$[\alpha]_D^{27}$: $-84.4°$ (1N-NaOH)
Elemental analysis for $C_{28}H_{40}N_4O_8 \cdot 1.5H_2O$: Calculated (%): C: 57.23; H: 7.38, N: 9.53. Found (%): C: 57.33, H: 7.67, N: 9.64.

1-(D-Prolyl-L-lysyl-gamma-D-glutamyl)indoline-2(S)-carboxylic acid (Example 17):
Melting point: 209°-216° C. (decomp.)
$[\alpha]_D^{30}$: $-66.3°$ (1N-NaOH)
Elemental analysis for $C_{25}H_{35}N_5O_7 \cdot 3.5H_2O$: Calculated (%): C: 51.71, H: 7.29, N: 12.06. Found (%): C: 51.58, H: 7.40, N: 12.08.

(2S,3aS,7aS)-1-($N^2$-Cyclobutanecarbonyl-L-lysl-gamma-D-glutamyl)octahydro-1H-indole-2-carboxylic acid (Example 18):

[α]$_D^{23}$: −46.8° (1N-NaOH)

Elemental analysis for $C_{25}H_{40}N_5O_7.2H_2O.0.25C_4H_8O_2$: Calculated (%): C: 55.11, H: 8.18, N: 9.89 Found (%): C: 55.16, H: 7.98, N: 9.78

1-(L-Pyroglutamyl-L-lysyl-gamma-D-glutamyl)indoline-2(S)-carboxylic acid (Example 19):

[α]$_D^{25}$: −81.0° (1N-NaOH)

Elemental analysis for $C_{25}H_{33}N_5O_8.3.25H_2O$: Calculated (%): C: 50.88, H: 6.75, N: 11.87. Found (%): C: 50.85, H: 6.56, N: 11.96.

(2S,3aS,7aS)-1-[N$^2$-(Pyridine-2-carbonyl)-L-lysyl-gamma-D-glutamyl]octahydro-1H-indole-2-carboxylic acid (Example 20):

[α]$_D^{25}$: −19.2° (H$_2$O)

Elemental analysis for $C_{26}H_{37}N_5O_7.1.75H_2O$: Calculated (%): C: 55.45, H: 7.25, N: 12.44. Found (%): C: 55.74, H: 7.05, N: 12.42.

(2S,3aS,7aS)-1-[N$^2$-(4-Metoxybenzoyl-L-lysyl-gamma-D-glutamyl]octahydro-1H-indole-2-carboxylic acid (Example 21):

[α]$_D^{26}$: −15.2° (H$_2$O)

Elemental analysis for $C_{28}H_{40}N_4O_8.3.5H_2O$: Calculated (%): C: 53.92, H: 7.60, N: 8.98. Found (%): C: 53.77, H: 7.33, N: 9.13.

(2S,3aS,7aS)-1-(N$^2$-Nicotinoyl-D-lysyl-gamma-D-glutamyl)octahydro-1H-indole-2-carboxylic acid (Exampe 22):

[α]$_D^{28}$: −26.5° (1N-NaOH)

Elemental analysis for $C_{26}H_{37}N_5O_7.2.25H_2O$: Calculated (%): C: 54.58, H: 7.31, N: 12.24. Found (%): C: 54.37, H: 7.39, N: 12.29.

EXAMPLE 23

(2S,3aS,7aS)-1-[N$^2$-Benzylcarbamoyl)-L-lysyl-gamma-D-glutamyl]octahydro-1H-indole-2-carboxylic acid In 5 ml of pyridine was dissolved 0.56 g of (2S,3aS,7aS)-1-(N$^6$-benzyloxycarbonyl-L-lysyl-gamma-D-glutamyl)octahydro-1H-indole-2-carboxylic acid, and 0.14 g of benzyl isocyanate was added. The mixture was stirred overnight at room temperature. A sodium bicarbonate solution was added, and the mixture was washed with ethyl acetate. The aqueous layer was acidified with 10% citric acid, and extracted with ethyl acetate. The organic layer was washed with brine, dried and concentrated to dryness under reduced pressure to give 0.66 g of a powder. In 15 ml of methanol was dissolved 0.65 g of the resulting powder, and 0.3 g of ammonium formate and 0.1 g of 10% palladium-carbon were added. The mixture was stirred at 60° C. for 40 minutes. The catalyst was removed, and the solvent evaporated. The residue was subjected to CHP20P column chromatography (0%→50% acetonitrile/water gradient). Fractions containing the desired product were concentrated to dryness under reduced pressure, and the residue was lyophilized to give 0.109 g of the captioned compound.

[α]$_D^{32}$: −32.0° (1N-NaOH)

Elemental analysis for $C_{28}H_{41}N_5O_7.2H_2O$: Calculated (%): C: 56.46, H: 7.61, N: 11.76. Found (%): C: 56.39, H: 7.32, N: 11.41.

EXAMPLES 24–25

The following compounds were synthesized in the same way as in Example 23.

(2S,3aS,7aS)-1-[N$^2$-Cyclohexylcarbamoyl)-L-lysyl-gamma-D-glutamyl]octahydro-1H-indole-2-carboxylic acid (Example 24):

[α]$_D^{29}$: −31.1° (1N-NaOH)

Elemental analysis for $C_{27}H_{45}N_5O_7.1.25H_2O.0.25C_4H_8O_2$: Calculated (%): C: 56.41, H: 8.37, N: 11.75. Found (%): C: 56.23, H: 8.07, N: 11.67.

(2S,3aS,7aS)-1-[N$^2$-Phenylcarbamoyl)-L-lysyl-gamma-D-glutamyl]octahydro-1H-indole-2-carboxylic acid (Example 25):

[α]$_D^{32}$: −42.0° (1N-NaOH)

Elemental analysis for $C_{27}H_{39}N_5O_7.1.5H_2O$: Calculated (%): C: 56.63, H: 7.39, N: 12.23 Found (%): C: 56.80, H: 7.23, N: 12.03

EXAMPLE 26

(2S,3aS,7aS)-1-[N$^2$-Phenethyloxycarbonyl-L-lysyl-gamma-D-glutamyl]octahydro-1H-indole-2-carboxylic acid N,N'-disuccininyl carbonate (5.12 g), 2.44 g of phenethyl alcohol and 0.49 g of 4-dimethylaminopyridine were stirred in methylene choride for 3 days. The reaction mixture was washed with water, dried over anhydrous sodium sulfate and concentrated to dryness under reduced pressure. The residue was crystallized from ether. The crystals were collected by filtration to give 3.5 g of N-(phenethyloxycarbonyloxy)succinimide (mp. 69°–72° C.). N$^6$-t-butoxycarbonyl-L-lysine (2.53 g) was dissolved in a mixture of 30 ml of acetonitrile and 50 ml of 5% potassium carbonate, and 2.9 g of N-(phenethyloxycarbonyloxy)succinimide was added. The mixture was stirred at room temperature for 1 hour. The reaction mixture was washed with chloroform. The aqueous layer was acidified with 10% citric acid, and extracted with chloroform. The extract was dried over anhydrous sodium sulfate, and concentrated to dryness under reduced pressure to give 4.5 g of N$^6$-t-butoxycarbonyl-N$^2$-phenethyloxycarbonyl-L-lysine as an oily substance. An aliquot (1.26 g) of the oily substance and N,N'-disuccinimidyl carbonate were stirred in ethyl acetate for 3 hours, and then an ethyl acetate solution containing 1.0 g of (2S,3aS,7aS)-1-(gamma-D-glutamyl)octahydro-1H-indole-2-carboxylic acid and 0.256 g of pyridine was added, and the mixture was further stirred for 5 hours. The reaction mixture was extracted with 5% sodium bicarbonate solution. The extract was acidified with 10% citric acid, and extracted with ethyl acetate. The organic layer was dried over anhydrous sodium sulfate, and concentrated to dryness under reduced pressure. The residue was dissolved in 20 ml of trifluoroacetic acid, left to stand at room temperature for 20 minutes, and thereafter concentrated to dryness under reduced pressure. The residue was subjected to CHP20P column chromatography (0%→60% acetonitrile/water gradient). Fractions containing the desired product were concentrated to dryness under reduced pressure. The residue dissolved in dioxane/water, and lyophilized to give 0.3 g of the captioned compound.

[α]$_D^{32}$: −36.9° (1N-NaOH)

Elemental analysis for $C_{29}H_{42}N_4O_8.2H_2O.0.25C_4H_8O_2$: Calculated (%): C: 56.95, H: 7.65, N: 8.85. Found (%): C: 56.92, H: 7.87, N: 8.64.

EXAMPLE 27

(2S,3aS,7aS)-1-(N$^2$-Benzoyl-L-lysyl-gamma-D-glutamyl)octahydro-1H-indole-2-carboxylic acid Sodium carbonate (2.0 g) was dissolved in 10 ml of water, and 4.83 g of (2S,3aS,7aS)-1-(gamma-D-glutamyl)octahydro-1H-indole-2-carboxylic acid was added. After a solution formed, 40 ml of tetrahydrofuran was added. With vigorous stirring, 7.46 g of N$^2$-benzyloxycarbonyl-$N^6$-t-butoxycarbonyl-L-lysine N-hydroxysuccinimide ester was gradually added. The mixture was stirred overnight at room temperature. The reaction mixture was half concentrated, acidified with 10% citric acid, and extracted with ethyl acetate. The organic layer was washed with saturated aqueous sodium chloride solution, dried over anhydrous sodium sulfate, and concentrated to dryness under reduced pressure to give 9.17 g of (2S,3aS,7aS)-1-($N^2$-benzyloxycarbonyl-$N^6$-butoxycarbonyl-L-lysyl-gamma-D-glutamyl)octahydro-1H-indole-2-carboxylic acid.

(2) An aliquot (6.2 g) of the resulting carboxylic acid was dissolved in 60 ml of ethanol, and 1.0 g of 10% palladium-carbon was added. With stirring, 2.5 of ammonium formate was added little by little. The mixture was stirred for 4 hours. The catalyst was removed by filtration. The mother liquor was concentrated to dryness, and ethyl acetate was added to the residue. The resulting powder was collected by filtration to give 3.9 g of (2S,3aS,7aS)-1-($N^6$-t-butoxycarbonyl-L-lysyl-gamma-D-glutamyl)-octahydro-1H-indole-2-carboxylic acid.

An aliquot (1.0 g) of the resulting carboxylic acid was dissolved in 7 ml of water, and 0.55 g of sodium bicarbonate and 12 ml of THF added. With vigorous stirring, 0.46 of N-benzoyloxysuccinimde was added, and the mixture was stirred overnight at room temperature. The reaction mixture was half concentrated, acidified with 10% citric acid, and extracted with methylene chloride. The organic layer was washed with water, dried over anhydrous sodium sulfate, and concentrated to dryness under reduced pressure.

(4) To the residue was added 20 ml of trifluoroacetic acid under ice cooling, and the mixture was stirred for 15 minutes. Trifluoroacetic acid was evaporated under reduced pressure. The residue was chromatographed on a column of CHP20P using acetonitrile/water (0%→50% gradient). Fractions containing the desired product were concentrated to dryness under reduced pressure. The residue was lyophilized to give 0.50 g of the captioned compound.

$[\alpha]_D^{25}$: $-23.1°$ ($H_2O$)

Elemental analysis for $C_{27}H_{38}N_4O_7.2.25H_2O$: Calculated (%): C: 56.78, H: 7.50, N: 9.81 Found (%): C: 56.91, H: 7.29, N: 10.03

EXAMPLES 28–50

The following compounds were synthesized in the same way as in Example 27.

1-[$N^2$-(4-Methoxyphenylethoxycarbonyl)-L-lysyl-gamma-D-glutamyl]indoline-2(S)-carboxylic acid (Example 28):
Melting point: 197°–202° C.
$[\alpha]_D^{31}$: $-74.2°$ (1N-NaOH)
Elemental analysis for $C_{30}H_{37}N_4O_9.H_2O$: Calculated (%): C: 58.53, H: 6.39, N: 9.10. Found (%): C: 58.53, H: 6.43, N: 9.14.

(2S,3aS,7aS)-1-($N^2$-Isonicotinoyl-L-lysyl-gamma-D-glutamyl)octoahydro-1H-indole-2-carboxylic acid (Example 29):
$[\alpha]_D^{25}$: $-29.8°$ ($H_2O$)
Elemental analysis for $C_{26}H_{37}N_5O_7.2.5H_2O$: Calculated (%): C: 54.16, H: 7.34, N: 12.15. Found (%): C: 54.25, H: 7.06, N: 12.23.

(2S,3aS,7aS)-1-($N^2$-Cyclopentyloxycarbonyl-L-lysyl-gamma-D-glytamyl)octahydro-1H-indole-2-carboxylic acid (Example 30):
$[\alpha]_D^{25}$: $-37.1°$ ($H_2O$)
Elemental analysis for $C_{26}H_{42}N_4O_8.1.5H_2O$: Calculated (%): C: 55.21, H: 8.02, N: 9.90. Found (%): C: 55.05, H: 7.77, N: 10.05.

(2S,3aS,7aS)-1-($N^2$-Cyclohexyloxycarbonyl-L-lysyl-gamma-D-glutamyl)octahydro-1H-indole-2-carboxylic acid (Example 31):
$[\alpha]_D^{25}$: $-31.9°$ ($H_2O$)
Elemental analysis for $C_{27}H_{44}N_4O_8.1.75H_2O$: Calculated (%): C: 55.51, H: 8.20, N: 9.59. Found (%): C: 55.53, H: 8.42, N: 9.55.

(2S,3aS,7aS)-1-[$N^2$-(Cyclobutyloxycarbonyl)-L-lysyl-gamma-D-glutamyl]octahydro-1H-indole-2-carboxylic acid (Example 32):
$[\alpha]_D^{25}$: $-40.7°$ ($H_2O$)
Elemental analysis for $C_{25}H_{40}N_4O_8.2H_2O$: Calculated (%): C: 53.56, H: 7.91, N: 9.99. Found (%): C: 53.57, H: 7.60, N: 9.93.

1-($N^2$-Cyclobutyloxycarbonyl-L-lysyl-gamma-D-glutamyl)indoline-2(S)-carboxylic acid (Example 33):
Melting point: 197°–204° C.
$[\alpha]_D^{27}$: $-84.0°$ (1N-NaOH)
Elemental analysis for $C_{25}H_{34}N_4O_8.1.75H_2O$: Calculated (%): C: 54.49, H: 7.12, N: 9.78. Found (%): C: 54.67, H: 7.40, N: 9.53.

1-($N^2$-Cyclohexylethoxycarbonyl-L-lysyl-gamma-D-glutamyl)indoline-2(S)-carboxylic acid (Example 34):
Melting point: 192°–195° C.
$[\alpha]_D^{31}$: $-78.8°$ (1N-NaOH)
Elemental analysis for $C_{29}H_{42}N_4O_8.1.5H_2O$: Calculated (%): C: 57.89, H: 7.54, N: 9.31. Found (%): C: 57.82, H: 7.74, N: 9.36.

1-($N^2$-Nicotinoyl-L-lysyl-gamma-D-glutamyl)indoline-2(S)-carboxylic acid (Example 35):
Melting point: 218°–222° C.
$[\alpha]_D^{31}$: $-66.5°$ (1N-NaOH)
Elemental analysis for $C_{26}H_{31}N_5O_7.2.25H_2O$: Calculated (%): C: 55.16, H: 6.32, N: 12.37. Found (%): C: 55.24, H: 6.57, N: 12.24.

1-($N^2$-Cyclobutanecarbonyl-L-lysyl-gamma-D-glutamyl)-indoline-2(S)-carboxylic acid (Example 36):
Melting point: 209°–215° C.
$[\alpha]_D^{24}$: $-96.6°$ (1N-NaOH)
Elemental analysis for $C_{25}H_{34}N_4O_7.1.5H_2O$: Calculated (%): C: 56.70, H: 7.04, N: 10.58. Found (%): C: 56.64, H: 7.06, N: 10.46.

1-($N^2$-Cyclopentyloxycarbonyl-L-lysyl-gamma-D-glutamyl)indoline-2(S)-carboxylic acid (Example 37):
Melting point: 198°–203° C.
$[\alpha]_D^{24}$: $-79.3°$ (1N-NaOH)
Elemental analysis for $C_{26}H_{36}N_4O_8.2.25H_2O$: Calculated (%): C: 54.49, H: 7.12, N: 9.78. Found (%): C: 54.67, H: 7.40, N: 9.53.

1-[$N^2$-(2-Pyridineethoxycarbonyl)-L-lysyl-gamma-D-glutamyl]indoline-2(S)-carboxylic acid (Example 38):
$[\alpha]_D^{28}$: $-69.3°$ (1N-NaOH)
Elemental analysis for $C_{28}H_{35}N_5O_8.2.25H_2O$: Calculated (%): C: 55.12, H: 6.53, N: 11.48. Found (%): C: 54.91, H: 6.37, N: 11.33.

1-($N^2$-Benzoyl-L-lysyl-gamma-D-glutamyl)indoline-2(S)-carboxylic acid (Example 39):
Melting point: 202°–208° C.
$[\alpha]_D^{24}$: $-77.2°$ (1N-NaOH)
Elemental analysis for $C_{27}H_{32}N_4O_7.2H_2O$: Calculated (%): C: 57.85, H: 6.47, N: 9.99. Found (%): C: 57.97, H: 6.32, N: 10.20.

1-[N²-(4-Morpholineethoxycarbonyl)-L-lysyl-gamma-D-glutamyl]indoline-2(S)-carboxylic acid (Example 40):

$[\alpha]_D^{25}$: −57.4° (1N-NaOH)

Elemental analysis for $C_{27}H_{35}N_5O_8 \cdot 2.25H_2O$: Calculated (%): C: 48.57, H: 7.40, N: 10.49. Found (%): C: 48.70, H: 7.23, N: 10.45.

1-[N²-(3-Pyridinemethoxycarbonyl)-L-lysyl-gamma-D-glutamyl]indoline-2(S)-carboxylic acid (Example 41):

$[\alpha]_D^{25}$: −64.2° (1N-NaOH)

Elemental analysis for $C_{27}H_{33}N_5O_8 \cdot 2.75H_2O$: Calculated (%): C: 53.59, H: 6.41, N: 11.57. Found (%): C: 53.41, H: 6.14, N: 11.56.

(2S,3aS,7aS)-1-[N²-(4-Chlorobenzyloxycarbonyl)-L-lysyl-gamma-D-glutamyl]octahydro-1H-indole-2-carboxylic acid (Example 42):

$[\alpha]_D^{32}$: −30.8° (1N-NaOH)

Elemental analysis for $C_{28}H_{39}ClN_4O_8 \cdot 1.5H_2O$: Calculated (%): C: 54.06, H: 6.81, N: 9.01, Cl: 5.70 Found (%): C: 53.95, H: 6.65, N: 8.80, Cl: 5.56

(2S,3aS,7aS)-1-[N²-(4-Methylbenzyloxycarbonyl)-L-lysyl-gamma-D-glutamyl]octahydro-1H-indole-2-carboxylic acid (Example 43):

$[\alpha]_D^{32}$: −31.9° (1N-NaOH)

Elemental analysis for $C_{29}H_{42}N_4O_8 \cdot 1.75H_2O$: Calculated (%): C: 57.46, H: 7.57, N: 9.24. Found (%): C: 57.37, H: 7.51, N: 9.07.

(2S,3aS,7aS)-1-[N²-(2-Chlorobenzyloxycarbonyl)-L-lysyl-gamma-D-glutamyl]octahydro-1H-indole-2-carboxylic acid (Example 44):

$[\alpha]_D^{32}$: −32.8° (1N-NaOH)

Elemental analysis for $C_{28}H_{39}ClN_4O_8 \cdot 1.25H_2O$: Calculated (%): C: 54.45, H: 6.77, N: 9.07, Cl: 5.74. Found (%): C: 54.55, H: 6.81, N: 8.90, Cl: 5.60.

(2S,3aS,7aS)-1-[N²-(2-Methylbenzyloxycarbonyl)-L-lysyl-gamma-D-glutamyl]octahydro-1H-indole-2-carboxylic acid (Example 45):

$[\alpha]_D^{32}$: −35.8° (1N-NaOH)

Elemental analysis for $C_{29}H_{42}N_4O_8 \cdot 1.75H_2O$: Calculated (%): C: 57.46, H: 7.57, N: 9.24. Found (%): C: 57.68, H: 7.63, N: 9.01.

(2S,3aS,7aS)-1-[N²-(2-Fluorobenzyloxycarbonyl)-L-lysyl-gamma-D-glutamyl]octahydro-1H-indole-2-carboxylic acid (Example 46):

$[\alpha]_D^{32}$: −32.5° (1N-NaOH)

Elemental analysis for $C_{28}H_{39}FN_4O_8 \cdot 1.5H_2O \cdot 0.5C_4H_8O_2$: Calculated (%): C: 55.46, H: 7.14, N: 8.62, F: 2.92 Found (%): C: 55.63, H: 7.08, N: 8.54, F: 3.01

(2S,3aS,7aS)-1-[N²-(alpha-Naphthylmehoxycarbonyl)-L-lysyl-gamma-D-glutamyl]octahydro-1H-indole-2-carboxylic acid (Example 47):

$[\alpha]_D^{32}$: −36.3° (1N-NaOH)

Elemental analysis for $C_{32}H_{42}N_4O_8 \cdot 1.5H_2O \cdot 0.25C_4H_8O_2$: Calculated (%): C: 60.08, H: 7.18, N: 8.49. Found (%): C: 59.78, H: 7.41, N: 8.37.

(2S,3aS,7aS)-1-[N²-(alpha-Naphthylethoxycarbonyl)-L-lysyl-gamma-D-glutamyl]octahydro-1H-indole-2-carboxylic acid (Example 48):

$[\alpha]_D^{32}$: −38.8° (1N-NaOH)

Elemental analysis for $C_{33}H_{44}N_4O_8 \cdot 2H_2O \cdot 0.5C_4H_8O_2$: Calculated (%): C: 59.64, H: 7.44, N: 7.95. Found (%): C: 59.87, H: 7.17, N: 7.91.

(2S,3aS,7aS)-1-[N²-(4-Phenylbenzyloxycarbonyl)-L-lysyl-gamma-D-glutamyl]octahydro-1H-indole-2-carboxylic acid (Example 49):

$[\alpha]_D^{27}$: −39.1° (1N-NaOH)

Elemental analysis for $C_{34}H_{44}N_4O_8 \cdot 1.5H_2O \cdot 0.5C_4H_8O_2$: Calculated (%): C: 61.09, H: 7.26, N: 7.92. Found (%): C: 61.23, H: 7.26, N: 7.85.

(2S,3aS,7aS)-1-[N²-(Phenoxycarbonyl-L-lysyl-gamma-D-glutamyl]octahydro-1H-indole-2-carboxylic acid (Example 50):

$[\alpha]_D^{29}$: −17.7° (1N-NaOH)

Elemental analysis for $C_{27}H_{38}N_4O_8 \cdot 1H_2O \cdot 0.5C_4H_8O_2$: Calculated (%): C: 57.22, H: 7.29, N: 9.20. Found (%): C: 56.95, H: 7.13, N: 9.49.

EXAMPLE 51

(2S,3aS,7aS)-1-[N²-(4-Hydroxybenzoyl)-L-lysyl-gamma-D-glutamyl)octahydro-1H-indole-2-carboxylic acid In 5 ml of water was dissolved 1.30 g of (2S,3aS,7aS)-1-(N⁶-benzyloxycarbonyl-L-lysyl-gamma-D-glutamyl)octahydro-1H-indole-2-carboxylic acid, and 0.25 g of sodium carbonate and 10 ml of tetrahydrofuran were added. With vigorous stirring, 0.7 g of N-(4-hydroxybenzoyloxy)succinimide was added, and the mixture was stirred overnight at room temperature. The reaction mixture was half concentrated, acidified with 10% citric acid, and extracted with methylene chloride. The organic layer was washed with water, dried over anhydrous sodium sulfate, and concentrated to dryness under reduced pressure. The residue was chromatographed on a column of CHP20P (2.5 cm in diameter and 40 cm in length) using acetonitrile/water (30%→70% gradient) as an eluent. Fractions containing the desired product were concentrated to dryness under reduced pressure to give 0.6 g of a residue. The residue was dissolved in 25% HBr/AcOH (10 ml), and the mixture was stirred at room temperature for 1 hour. Then, 100 ml of ether was added, and the resulting white precipitate was collected by filtration, and chromatographed on a column of CHP2OP; 2.5 cm in diameter and 40 cm in length) using acetonitrile/water (0%→40% gradient). Fractions containing the desired product were concentrated to dryness under reduced pressure. The residue was lyophilized to obtain 0.3 g of the captioned compound.

$[\alpha]_D^{27}$: −17.4° ($H_2O$)

Elemental analysis for $C_{27}H_{38}N_4O_8 \cdot 1.5H_2O$: Calculated (%): C: 56.53, H: 7.20, N: 9.77. Found (%): C: 56.71, H: 7.09, N: 9.95.

EXAMPLES 52-67

The following compounds were synthesized in the same way as in Example 51.

(2S,3aS,7aS)-1-[N²-(2-Thiophenecarbonyl)-L-lysyl-gamma-D-glutamyl]octahydro-1H-indole-2-carboxylic acid (Example 52):

$[\alpha]_D^{26}$: −23.1° ($H_2O$)

Elemental analysis for $C_{25}H_{36}N_4O_7S \cdot H_2O$: Calculated (%): C: 54.14, H: 6.91, N: 10.10, S: 5.78. Found (%): C: 54.09, H: 6.74, N: 10.14, S: 5.99.

(2S,3aS,7aS)-1-[N²-(3-Quinolinecarbonyl)-L-lysyl-gamma-D-glutamyl]octahydro-1H-indole-2-carboxylic acid (Example 53):

$[\alpha]_D^{24}$: −25.8° (1N-NaOH)

Elemental analysis for $C_{30}H_{39}N_5O_7 \cdot 2H_2O$: Calculated (%): C: 58.33, H: 7.02, N: 11.34. Found (%): C: 58.46, H: 7.30, N: 11.24.

(2S,3aS,7aS)-1-[N²-(2-Chloronicotinoyl)-L-lysyl-gamma-D-glutamyl]octahydro-1H-indole-2-carboxylic acid (Example 54):

$[\alpha]_D^{26}$: −42.6° ($H_2O$)

Elemental analysis for $C_{26}H_{38}ClN_5O_7.1.5H_2O$: Calculated (%): C: 52.66, H: 6.63, N: 11.81, Cl: 5.98. Found (%): C: 52.75, H: 6.68, N: 11.76, Cl: 5.89.

(2S,3aS,7aS)-1-[N$^2$-(4-Chlorobenzoyl)-L-lysyl-gamma-D-glutamyl]octahydro-1H-indole-2-carboxylic acid (Example 55):

$[\alpha]_D^{25}$: $-25.9°$ (1N-NaOH)

Elemental analysis for $C_{27}H_{37}ClN_4O_7.1.5H_2O$: Calculated (%): C: 54.77, H: 6.81, N: 9.46, Cl: 5.99. Found (%): C: 55.07, H: 7.09, N: 9.26; Cl: 5.79.

(2S,3aS,7aS)-1-[N$^2$-(Indoline-2(S)-carbonyl)-L-lysyl-gamma-D-glutamyl]octahydro-1H-indole-2-carboxylic acid (Example 56):

$[\alpha]_D^{25}$: $-64.3°$ (1N-NaOH)

Elemental analysis for $C_{29}H_{41}N_5O_9.2.25H_2O$: Calculated (%): C: 56.90, H: 7.47, N: 11.44. Found (%): C: 56.99, H: 7.61, N: 11.15.

(2S,3aS,7aS)-1-[N$^2$-(2-Thianaphthenecarbonyl)-L-lysyl-gamma-D-glutamyl]octahydro-1H-indole-2-carboxylic acid (Example 57):

$[\alpha]_D^{25}$: $-16.5°$ (1N-NaOH)

Elemental analysis for $C_{29}H_{38}N_4O_7S.2H_2O$: Calculated (%): C: 55.93, H: 6.80, N: 9.00, S: 5.15. Found (%): C: 56.08, H: 6.63, N: 8.87, S: 4.94.

(2S,3aS,7aS)-1-[N$^2$-(2-Quinoxalinecarbonyl)-L-lysyl-gamma-D-glutamyl]octahydro-1H-indole-2-carboxylic acid (Example 58):

$[\alpha]_D^{26}$: $-15.3°$ (1N-NaOH)

Elemental analysis for $C_{29}H_{38}N_6O_7.1.25H_2O$: Calculated (%): C: 57.56, H: 6.75, N: 13.89. Found (%): C: 57.48, H: 7.00, N: 13.96.

(2S,3aS,7aS)-1-[N$^2$-(2-Isoquinolinecarbonyl)-L-lysyl-gamma-D-glutamyl]octahydro-1H-indole-2-carboxylic acid (Example 59):

$[\alpha]_D^{26}$: $-51.8°$ (1N-NaOH)

Elemental analysis for $C_{30}H_{39}N_5O_7.1H_2O$: Calculated (%): C: 60.09, H: 6.89, N: 11.68. Found (%): C: 59.89, H: 6.66, N: 11.61.

(2S,3aS,7aS)-1-[N$^2$-(6-Methoxynicotinoyl)-L-lysyl-gamma-D-glutamyl]octahydro-1H-indole-2-carboxylic acid (Example 60):

$[\alpha]_D^{27}$: $-18.0°$ (H$_2$O)

Elemental analysis for $C_{27}H_{39}N_5O_8.1.5H_2O$: Calculated (%): C: 55.09, H: 7.19, N: 11.90. Found (%): C: 55.09, H: 7.44, N: 11.77.

(2S,3aS,7aS)-1-[N$^2$-(6-Ethoxynicotinoyl)-L-lysyl-gamma-D-glutamyl]octahydro-1H-indole-2-carboxylic acid (Example 61):

$[\alpha]_D^{27}$: $-16.4°$ (H$_2$O)

Elemental analysis for $C_{28}H_{41}N_5O_8.2H_2O$: Calculated (%): C: 54.98, H: 7.42, N: 11.45. Found (%): C: 55.00, H: 7.70, N: 11.27.

(2S,3aS,7aS)-1-[N$^2$-(6-Chloronicotinoyl)-L-lysyl-gamma-D-glutamyl]octahydro-1H-indole-2-carboxylic acid (Example 62):

$[\alpha]_D^{27}$: $-21.4°$ (H$_2$O)

Elemental analysis for $C_{26}H_{36}ClN_5O_7.2H_2O$: Calculated (%): C: 51.87, H: 6.70, N: 11.63, Cl: 5.89. Found (%): C: 51.78, H: 6.44, N: 11.86, Cl: 6.05.

(2S,3aS,7aS)-1-[N$^2$-(2-Hydroxybenzoyl)-L-lysyl-gamma-D-glutamyl]octahydro-1H-indole-2-carboxylic acid (Example 63):

$[\alpha]_D^{28}$: $-21.0°$ (H$_2$O)

Elemental analysis for $C_{27}H_{38}N_4O_8.1.25H_2O$: Calculated (%): C: 56.98, H: 7.17, N: 9.84. Found (%): C: 56.83, H: 7.26, N: 9.89.

(2S,3aS,7aS)-1-[N$^2$-(6-n-Propoxynicotinoyl)-L-lysyl-gamma-D-glutamyl]octahydro-1H-indole-2-carboxylic acid (Example 64):

$[\alpha]_D^{31}$: $-25.2°$ (1N-NaOH)

Elemental analysis for $C_{29}H_{43}N_5O_8.1.5H_2O$: Calculated (%): C: 56.48, H: 7.52, N: 11.36. Found (%): C: 56.56, H: 7.22, N: 11.36.

(2S,3aS,7aS)-1-[N$^2$-(2-i-Propoxynicotinoyl)-L-lysyl-gamma-D-glutamyl]octahydro-1H-indole-2-carboxylic acid (Example 65):

$[\alpha]_D^{31}$: $-26.4°$ (1N-NaOH)

Elemental analysis for $C_{29}H_{43}N_5O_8.2H_2O$: Calculated (%): C: 55.67, H: 7.57, N: 11.19. Found (%): C: 55.41, H: 7.80, N: 11.05.

(2S,3aS,7aS)-1-[N$^2$-(3-Hydroxybenzoyl)-L-lysyl-gamma-D-glutamyl]octahydro-1H-indole-2-carboxylic acid (Example 66):

$[\alpha]_D^{31}$: $-29.8°$ (1N-NaOH)

Elemental analysis for $C_{27}H_{38}N_4O_8.1.25H_2O$: Calculated (%): C: 56.98, H: 7.17, N: 9.84. Found (%): C: 57.07, H: 7.16, N: 9.79.

(2S,3aS,7aS)-1-[N$^2$-(4-Hydroxy-3-methoxybenzoyl)-L-lysyl-gamma-D-glutamyl]octahydro-1H-indole-2-carboxylic acid (Example 67-1):

$[\alpha]_D^{28}$: $-17.9°$ (H$_2$O)

Elemental analysis for $C_{28}H_{40}N_4O_9.2H_2O$: Calculated (%): C: 54.89, H: 7.24, N: 9.14. Found (%): C: 54.95, H: 7.26, N: 9.04.

(2S,3aS,7aS)-1-[N$^2$-(3-Hydroxy-4-methoxybenzoyl)-L-lysyl-gamma-D-glutamyl]octahydro-1H-indole-2-carboxylic acid (Example 67-2):

$[\alpha]_D^{31}$: $-40.0°$ (1N-NaOH)

Elemental analysis for $C_{28}H_{40}N_4O_9.3.25H_2O$: Calculated (%): C: 52.95, H: 7.38, N: 8.82. Found (%): C: 52.86, H: 7.07, N: 8.97.

(2S,3aS,7aS)-1-N$^2$-(2-Hydroxy-4-methylenzoyl)-L-lysyl-gamma-D-glutamyl]octahydro-1H-indole-2-carboxylic acid (Example 67-3):

$[\alpha]_D^{25}$: $+37.4°$ (1N-NaOH)

Elemental analysis for $C_{28}H_{40}N_4O_8.1H_2O$: Calculated (%): C: 58.12, H: 7.32, N: 9.68. Found (%): C: 57.92, H: 7.12, N: 9.46.

(2S,3aS,7aS)-1-[N$^2$-(6-Hydroxy-beta-naphthoyl)-L-lysyl-gamma-D-glutamyl]octahydro-1H-indole-2-carboxylic acid (Example 67-4):

$[\alpha]_D^{31}$: $-2.8°$ (1N-NaOH)

Elemental analysis for $C_{31}H_{40}N_4O_8.2.5H_2O$: Calculated (%): C: 58.02, H: 7.07, N: 8.73. Found (%): C: 57.90, H: 7.09, N: 8.58.

(2S,3aS,7aS)-1-[N$^2$-(3,5-Dimethyoxy-4-hydroxybenzoyl)-L-lysyl-gamma-D-glutamyl]octahydro-1H-indole-2-carboxylic acid (Example 67-5):

$[\alpha]_D^{26}$: $-4.1°$ (1N-NaOH)

Elemental analysis for $C_{29}H_{42}N_4O_{10}.2.5H_2O$: Calculated (%): C: 53.45, H: 7.27, N: 8.60. Found (%): C: 53.57, H: 7.24, N: 8.77.

(2S,3aS,7aS)-1-[N$^2$-(3-Hydroxy-2-naphthoyl)-L-lysyl-gamma-D-glutamyl)octahydro-1H-indole-2-carboxylic acid (Example 67-6):

$[\alpha]_D^{26}$: $+15.6°$ (1N-NaOH)

Elemental analysis for $C_{31}H_{40}N_4O_8.2.5H_2O$: Calculated (%): C: 58.02, H: 7.07, N: 8.73. Found (%): C: 57.82, H: 6.74, N: 8.47.

(2S,3aS,7aS)-1-[N$^2$-(2-Hydroxy-5-methoxybenzoyl)-L-lysyl-gamma-D-glutamyl]octahydro-1H-indole-2-carboxylic acid (Example 67-7):

$[\alpha]_D^{26}$: $+22.1°$ (1N-NaOH)

Elemental analysis for $C_{28}H_{40}N_4O_9 \cdot 1.5H_2O$: Calculated (%): C: 55.71, H: 7.18, N: 9.28. Found (%): C: 55.56, H: 7.09, N: 9.31.

(2S,3aS,7aS)-1-[$N^2$-(4-Hydroxy-3-aminobenzoyl)-L-lysyl-gamma-D-glutamyl]octahydro-1H-indole-2-carboxylic acid (Example 67-8):

$[\alpha]_D^{26}$: $-15.3°$ ($H_2O$)

Elemental analysis for $C_{27}H_{39}N_5O_8 \cdot 1.75H_2O$: Calculated (%): C: 54.67, H: 7.22, N: 11.81. Found (%): C: 54.81, H: 7.31, N: 11.79.

(2S,3aS,7aS)-1-[$N^2$-(2-Hydroxy-5-bromobenzoyl)-L-lysyl-gamma-D-glutamyl)octahydro-1H-indole-2-carboxylic acid (Example 67-9):

$[\alpha]_D^{26}$: $+10.8°$ (1N-NaOH)

Elemental analysis for $C_{27}H_{37}N_4O_8Br \cdot 1.75H_2O$: Calculated (%): C: 49.36, H: 6.21, N: 8.53, Br: 12.16. Found (%): C: 49.42, H: 6.25, N: 8.50, Br: 12.01.

(2S,3aS,7aS)-1-[$N^2$-(2-Hydroxy-5-methylbenzoyl)-L-lysyl-gamma-D-glutamyl)octahydro-1H-indole-2-carboxylic acid (Example 67-10):

$[\alpha]_D^{28}$: $+23.2°$ (1N-NaOH)

Elemental analysis for $C_{30}H_{42}N_4O_9 \cdot 1.25H_2O$: Calculated (%): C: 57.63, H: 7.17, N: 8.96. Found (%): C: 57.51, H: 7.20, N: 8.88.

(2S,3,aS,7aS)-1-[$N^2$-(2-Hydroxy-6-methoxybenzoyl)-L-lysyl-gamma-D-glutamyl)octahydro-1H-indole-2-carboxylic acid (Example 67-11):

$[\alpha]_D^{25}$: $+45.2°$ (1N-NaOH)

Elemental analysis for $C_{30}H_{42}N_4O_9 \cdot 1.5H_2O$: Calculated (%): C: 57.22, H: 7.20, N: 8.90. Found (%): C: 57.81, H: 7.25, N: 8.81.

(2S,3aS,7aS)-1-[$N^2$-(2-Hydroxy-4-chlorobenzoyl)-L-lysyl-gamma-D-glutamyl)octahydro-1H-indole-2-carboxylic acid (Example 67-12):

$[\alpha]_D^{30}$: $+29.3°$ (1N-NaOH)

Elemental analysis for $C_{27}H_{37}ClN_4O_8 \cdot 1.5H_2O$: Calculated (%): C: 53.33, H: 6.63, N: 9.21, Cl: 5.83. Found (%): C, 53.41, H: 6.72, N: 9.18, Cl: 5.79.

(2S,3aS,7aS)-1-[$N^2$-(2-Hydroxy-5-chlorobenzoyl)-L-lysyl-gamma-D-glutamyl)octahydro-1H-indole-2-carboxylic acid (Example 67-13):

$[\alpha]_D^{30}$: $+17.2°$ (1N-NaOH) Elemental analysis for $C_{27}H_{37}ClN_4O_8 \cdot 1.5H_2O$: Calculated (%): C: 53.33, H: 6.63, N: 9.21, Cl: 5.83. Found (%): C: 53.21, H: 6.75, N: b 9.23, Cl: 5.65.

EXAMPLE 68

1-($N^2$-Pyrazinoyl-L-lysyl-gamma-D-glutamyl)indoline-2(S)-carboxylic acid (1) Pyrazinoic acid (0.26 g) was dissolved in a mixure of 3 ml of dimethylformamide and 20 ml of methylene chloride, and 1.1 g of ethyl 1-($N^6$-t-butoxycarbonyl-L-lysyl-$O^1$-ethyl-gamma-D-glutamyl indoline-2(S)-carboxylate and 0.84 g of 1-ethyl-3-(3-dimethylaminopropyl)carbodiimide hydrochloride where added. The mixture was stirred overnight at room temperature. The reaction mixture was successively washed with saturafted aqueous sodium bicarbonate solution and water, dried over anhydorus sodium sulfate, and concentrated to dryness under reduced pressure. The residue was subjected to silica gel column chromatography (2% methanol/chloroform) to give 0.8 g of ethyl 1-($N^6$-t-butoxycarbonyl-$N^2$-pyrazinoyl-L-lysyl-$O^1$-ethyl-gamma-D-glutamyl)indoline-2(S)-carboxylate as a viscous oily substance.

(2) The compound obtained in (1) (0.8 g) was dissolved in dioxane, and 3.5 ml of 1N-NaOH was added. The mixture was stirred under ice cooling for 1.5 hours. The reaction mixture was concentrated, acidified with 10% citric acid, and chromatographed on a column of CHP20P using acetonitrile/water (0%→60% gradient) as an eluent. Fractions containing the desired product were concentrated to dryness under reduced pressure. The residue was re-precipitated from petroleum ether-/ethyl acetate. By filtration, 0.55 g of 1-($N^6$-t-butoxycaronyl-$N^2$-pyrazinoyl-L-lysyl-gamma-D-glutamyl)indoline-2(S)-carboxylic acid was obtained.

(3) Trifluoroacetic acid (10 ml) was added to an aliquot (0.45 g) of the final compound obtained in (2) above, and the mixture was stirred under ice cooling for 20 minutes. Trifluoroacetic was evaporated, and the residue was chromatographed on a column of CHP20P using acetonitrile/water (0%→30% gradient) as an eluent. Fractions containing the desired product were concentrated to dryness under reduced pressure, and the residue was lyophilized to give 0.27 g of the captioned compound.

$[\alpha]_D^{25}$: $-74.4°$ (1N-NaOH)

Elemental analysis for $C_{25}H_{30}N_6O_7 \cdot 2.5H_2O$: Calculated (%): C: 52.53; H: 6.17, N: 14.70. Found (%): C: 52.52, H: 6.27, N: 14.54.

EXAMPLE 69

Monosodium (2S,3aS,7aS)-1-($N^2$-nicotinoyl-L-lysyl-gamma-D-glutamyl)octahydro-1H-indole-2-carboxylate In 5 ml of water was dissolved 0.57 g of (2S,3aS,7aS)-1-($N^2$-nicotinoyl-L-lysyl-gamma-D-glutamyl)octahydro-1H-indole-2-carboxylic acid (see Example 15), and 1 ml of 1N-NaOH was added. The resulting aqueous solution was subjected to CHP20P column chromatography (0%→20% acetonitrile/water gradient). Fractions containing the desired product were concentrated to dryness under reduced pressure. The residue was lyophilized to give 0.25 g of the captioned compound.

$[\alpha]_D^{26}$: $-24.6°$ ($H_2O$).

EXAMPLE 70

(2S,3aS,7aS)-1-[$N^2$-(2-Methoxybenzoyl)-L-lysyl-gamma-D-glutamyl]octahydro-1H-indole-2-carboxylic acid (1) O-anisic acid (1.0 g), N-hydroxysuccinimide (0.76 g) and water-soluble carbodiimide hydrochloride (1.39 g) were dissolved in methylene chloride (15 ml), and the solution was stirred overnight at room temperature. The precipitate was removed by filtration. The mother liquor was concentrated under reduced pressure, and the residue was crystallized from isopropanol to give 1.47 g of N-(2-methoxybenzoyloxy)succinimide (mp. 180°-182° C.).

(2S,3aS,7aS)-1-($N^6$-benzyloxycarbonyl-L-lysyl-gamma-D-glutamyloctahydro-1H-indole-2carboxylic acid was dissolved in 6 ml of water, and sodium carbonate and 10 ml of THF were added. With vigorous stirring, N-(2-methoxybenzyloxy)succinimide was added. The mixture was stirred overnight at room temperature. The reaction mixture was acidified with 10% citric acid, and extracted with methylene chloride. The organic layer was dried over anhydrous sodium sulfate, and concentrated to dryness under reduced pressure. The residue was chromatographed on a column of CHP20P using acetonitrile/water (30%→70% gradient) as an eluent. Fractions containing the desired product were concentrated to dryness under reduced pressure to give 1.0 g of (2S,3aS,7aS)-1-[$N^6$-benzyloxycarbonyl-$N^2$-(2-methoxybenzoyl)-L-lysyl-gamma-D-glutamyl]octahydro-1H-indole-2-carboxylic acid.

(2) In 10 ml of ethanol was dissolved 1.0 g of (2S,3aS,7aS)-1-[N$^6$-benzyloxycarbonyl-N$^2$-(2-methoxybenzoyl)-L-lysyl-gamma-D-glutamyl]octahydro-1H-indole-2-carboxylic acid, and 1.18 g of cyclohexane and 0.2 g of 10% palladium-carbon were added. The mixture was stirred at 60° C. for 2 hours. The catalyst was removed by filtration, and the mother liquor was concentrated to dryness under reduced pressure. The residue was subjected to CHP20P column chromatography (0%→50% acetonitrile/water gradient). Fractions containing the desired product were concentrated under reduced pressure. The residue was lyophilized to give 0.34 g of the captioned compound.

$[\alpha]_D^{25}$: −14.9° (H$_2$O)

Elemental analysis for C$_{28}$H$_{40}$N$_4$O$_8$.2H$_2$O: Calculated (%): C: 56.36, H: 7.43, N: 9.39. Found (%): C: 56.63, H: 7.18, N: 9.33.

EXAMPLES 71–73

The following compounds were synthesized in the same way as in Example 70.

1-(N$^2$-Cyclohexylcarbonyl-L-lysyl-gamma-D-glutamyl)indoline-2(S)-carboxylic acid (Example 71):
Melting point: 207°–212° C.

$[\alpha]_D^{26}$: −90.3° (1N-NaOH)

Elemental analysis for C$_{27}$H$_{38}$N$_4$O$_7$.2H$_2$O: Calculated (%): C: 57.23, H: 7.47, N: 9.89. Found (%): C: 57.42, H: 7.52, H: 9.94.

(2S,3aS,7aS)-1-[N$^2$-(4-Phenylbenzoyl)-L-lysyl-gamma-D-glutamyl]octahydro-1H-indole-2-carboxylic acid (Example 72):

$[\alpha]_D^{26}$: −11.6° (1N-NaOH)

Elemental analysis for C$_{33}$H$_{42}$N$_4$O$_7$.1.5H$_2$O.0.5C$_8$O$_2$: Calculated (%): C: 62.02, H: 7.29, N: 8.27. Found (%): C: 61.98, H: 7.15, N: 8.35.

(2S,3aS,7aS)-1-[N$^2$-(4-Fluorobenzoyl)-L-lysyl-gamma-D-glutamyl]octahydro-1H-indole-2-carboxylic acid (Example 73):

$[\alpha]_D^{29}$: −31.8° (1N-NaOH)

Elemental analysis for C$_{27}$H$_{37}$N$_4$O$_7$F.2H$_2$O: Calculated (%): C: 55.47, H: 7.07, N: 9.58, F: 3.25. Found (%): C: 55.59, H: 7.36, N: 9.46, F: 3.03.

EXAMPLE 74

1-[N$^2$-(3,4-Methylenedioxybenzyloxycarbonyl)-L-lysyl-gamma-D-glutamyl]indoline-2(S)-carboxylic acid 2.5 g of N$^2$-t-butoxycarbonyl-N$^6$-(3-nitro-2-pyridinesulfenyl)-L-lysine and 2.2 g of ethyl 1-(O$^1$-ethyl-gamma-D-glutamyl)indoline-2(S)-carboxylic were dissolved in methylene chloride, and 2.0 g of 1-ethyl-3-(3-dimethylaminopropyl)-carbodiimide hydrochloride was added. The mixture was stirred overnight at room temperature. The reaction mixture was successively washed with saturated aqueous sodium bicarbonate solution, 5% aqueous potassium hydrogensulfate solution and aqueous sodium chloride solution, dried over anhydrous sodium sulfate, and concentrated to dryness under reduced pressure. The residue was recrystallized from ethanol to give 3.6 g of ethyl 1-[N$^2$-t-butoxycarbonyl-N$^6$-(3-nitro-2-pyridinesulfenyl)-L-lysyl-O$^1$-ethyl-gamma-D-glutamyl]indoline-2(S)-carboxylate. $[\alpha]_D^{27}$: −28.2° (dimethylformamide).

3.5 g of this ester was stirred with 30 ml of trifluoroacetic acid under ice cooling for 30 minutes. Trifluoroacetic acid was evporated, and ethyl acetate and 5% potassium carbonate were added to the residue. The mixture was vigorously shaken. The organic layer was washed with aqueous sodium chloride solution, dried over anhydrous sodium sulfate and concentrated under reduced pressure. The residue was recrystalized from ether/ethanol to give 2.6 g of ethyl 1-[N$^6$-(3-nitro-2-pyridinesulfenyl)-L-lysyl-O$^1$-ethyl-gamma-D-glutamyl]indoline-2(S)-carboxylate. mp. 95°–102° C. $[\alpha]_D^{27}$: −39.6° (dimethylformamide).

An aliquot (1.0 g) of the resulting ester was dissolved in 30 ml of methylene chloride, and 0.21 g of N-methylmorpholine and 1.07 g of N-(3,4-methylenedioxybenzyloxycarbonyloxy)succinimide were added, and the mixture was stirred at room temperature for 3 hours. The reaction mixture was washed successively with saturated aqueous sodium bicarbonate solution, 5% aqueous potassium hydrogensulfate solution, and water, dried over anhydrous sodium sulfate, and concentrated to dryness under reduced pressure. The residue was recrystallized from ethanol/methanol to give 1.1 g of ethyl 1-[N$^2$-(3,4-methylenedioxybenzyloxycarbonyl)-N$^6$-(3-nitro-2-pyridinesulfenyl)-L-lysyl-O$^1$-ethyl-gamma-D-glutamyl]indoline-2(S)-carboxylate. mp. 130°–135° C. $[\alpha]_D^{27}$: −23.2° (dimethylformamide).

An aliquot (1.0 g) of this product was worked up as in the second step of Example 68 to give 0.8 g of 1-[N$^2$-(3,4-methylenedioxybenzyloxycarbonyl)-N$^6$-(3-nitro-2-pyridinesulfenyl)-L-lysyl-gamma-D-glutamyl]indoline-2(S)-carboxylic acid. mp. 100°–110° C. $[\alpha]_D^{27}$: −70.5° (1N-NaOH).

An aliquot (0.74 g) of the product was dissolved in 10 ml of dioxane and 10 ml of 0.5N hydrochloric acid was added. The mixture was stirred at 45° C. for 4 hours. The reaction mixture was neutralized and concentrated, and the residue was acidified with 1N hydrochloric acid, and subjected to CHP20P column chromatography (0%→60% acetonitrile/water gradient). Fractions containing the desired product were concentrated, and the precipitated crystals were collected by filtration to give 45 mg of the captioned compound.

Melting point: 198°–202° C.

$[\alpha]_D^{27}$: −67.3° (1N-NaOH)

Elemental analysis for C$_{29}$H$_{34}$N$_4$O$_{10}$.2H$_2$O: Calculated (%): C: 54.88, H: 6.04, N: 8.83. Found (%): C: 55.16, H: 6.14, N: 8.83.

EXAMPLE 75

(2S,3aS,7aS)-1-[N-Benzyloxcarbonyl-S-(3-aminopropyl)-L-cysteinyl-gamma-D-glutamyl]octahydro-1H-indole-2-carboxylic acid L-cysteine hydrochloride hydrate (13 g) was dissolved in a mixture of 100 ml of ethanol and 50 ml of water, and 2N-NaOH was added. While the solution was maintained at a pH of 10, 16 g of 3-(t-butoxycarbonylamino)propyl bromide was added. The mixture was stirred at room temperature for 4 hours. After neutralization, the reaction mixture was concentrated to dryness under reduced pressure. The residue was dissolved in 15% aqueous ammonia, and subjected to CHP20P column chromatography (0%→30% acetonitrile/water gradient). Fractions containing the desired product were concentrated under reduced pressure. The precipitated crystals were collected by filtration to give 10.3 g of S-(3-t-butoxycarbonylaminopropyl)-L-cysteine. mp. 193° C. (decomp.) An aliquot (3.0 g) of the product was dissolved in a water/THF solution containing 3.0 g of potassium carbonate, and with vigorous stirring, 2.76 g of benzyloxycarbonyl chloride was added. The mixture was stirred at room temperature for 3 hours. The reaction mixture was washed with ether, acidified with 10% citric acid, and extracted with chloroform. The organic layer was dried over anhydrous sodium sulfate and concentrated under reduced pressure to give 2.8 g of N-benzyloxycarbonyl-S-(3-t-butoxycarbonylaminopropyl)-L-cysteine as an oil. The dicyclohexylamine salt of this compound had a melting point of 125° to 127° C. An aliquot (1.76 g) of the oily product was dissolved in 20 ml of acetonitrile, and 0.43 g of N-hydroxysuccinimide and 0.77 g of N,N-dicyclohexylcarbodiimide were added to the solution. The mixture was stirred for 2 hours. The precipitate was removed by filtration, and chloroform was added to the mother liquor. The mixture was washed successively with saturated aqueous sodium bicarbonate solution and aqueous sodium chloride solution, dried over anhydrous sodium sulfate, and concentrated to dryness under reduced pressure to give 2.2 g of a powder. Sodium bicarbonate (0.6 g) and 1.07 g of (2S,3aS,7aS)-1-(gamma-D-glutamyl)octahydro-1H-indole-2-carboxylic acid were dissolved in a mixture of 24 ml of THF and 12 ml of water, and 2.2 g of the above powder was added to the solution. The mixture was stirred at room temperature for 3 hours. The reaction mixture was neutralized and concentrated under reduced pressure. The residue was acidified wit 5% aqueous potassium hydrogen-sulfate solution and subjected to CHP20P column chromatography (30%→70% acetonitrile/water gradient). Fractions containing the desired product were concentrated under reduced pressure to give 0.6 g of (2S,3aS,7aS)-1-[N-benzyloxycarbonyl-S-(3-t-butoxycarbonylaminopropyl)-L-cysteinyl-gamma-D-glutamyl]octahydro-1H-indole-2-carboxylic acid. An aliquot (0.58 g) of this product was worked up as in the fourth step of Example 27 to give 0.33 g of the captioned compound.

$[\alpha]_D^{27}$: −26.7° (H$_2$O)

Elemental analysis for C$_{28}$H$_{40}$N$_4$O$_8$S.1H$_2$O: Calculated (%): C: 55.07, H: 6.93, N: 9.17, S: 5.25. Found (%): C: 55.00, H: 6.78, N: 9.16, S: 5.47.

EXAMPLE 76

(2S,3aS,7aS)-1-[N-Benzyloxycarbonyl-S-(3-aminopropyl)-L-cysteinyl-gamma-D-glutamyl]octahydro-1H-indole-2-carboxylic acid sulfoxide (2S,3aS,7aS)-1-[N-Benzyloxycarbonyl-S-(3-t-butoxycarbonylaminopropyl)-L-cysteinyl-gamma-D-glutamyl]octahydro-1H-indole-2-carboxylic acid (0.5 g) (see Example 75) was dissolved in methylene chloride, and 0.16 g of m-chloroperbenzoic acid was added. The mixture was stirred at room temperature for 1 hour. The reaction mixture was concentrated to dryness under reduced pressure. The residue was subjected to CHP20P column chromatography (30%→70% acetonitrile/water gradient). Fractions containing the desired product were concentrated to dryness under reduced pressure to give 0.33 g of a residue. The residue was worked up as in the fourth step of Example 27 to give 0.23 g of the captioned compound.

$[\alpha]_D^{24}$: −28.0° (1N-NaOH)

Elemental analysis for C$_{28}$H$_{40}$N$_4$O$_8$S.2H$_2$O: Calculated (%): C: 52.16, H: 6.88, N: 8.69, S: 4.97. Found (%): C: 52.29, H: 6.97, N: 8.82, S: 4.65.

EXAMPLE 77

(2S,3aS,7aS)-1-[N-Benzyloxycarbonyl-S-(2-aminoethyl)-L-cysteinyl-gamma-D-glutamyl]octahydro-1H-indole-2-carboxylic acid sulfoxide The captioned compound was synthesized in the same manner as in Example 76.

$[\alpha]_D^{28}$: −34.0° (1N-NaOH)

Elemental analysis for C$_{27}$H$_{38}$N$_4$O$_9$S.1H$_2$O: Calculated (%): C: 52.93, H: 6.58, N: 9.14, S: 5.23. Found (%): C: 52.60, H: 6.61; N: 9.29, S: 5.52.

EXAMPLE 78

1-N$^2$-Benzylcarbonyl-L-lysyl-gamma-D-glutamyl-L-proline

Sodium carbonate (1.8 g) and 2.97 g of alpha-ethyl D-glutamate were dissolved in water, and a THF solution of 8.9 g of N$^2$-benzyloxycarbonyl-N$^6$-t-butoxycarbonyl-L-lysine N-hydroxysucceinimide ester was added. The mixture was stirred overnight at room temperature. The reaction mixture was acidified with 5% aqueous potassium hydrogensulfate solution to a pH of 2 to 3, and then exracted with ethyl acetate. The extract was washed successively with 5% aqueous potassium hydrogen-sulfate solution and aqueous sodium chloride solution, dried, and concentrated to dryness under reduced pressure. The residue was crystallized from ether/petroleum ether. The crystals were collected by filtration to give 8.5 g of N$^2$-benzyloxycarbonyl-N$^6$-t-butoxycarbonyl-L-lysyl-O$^1$-ethyl-D-glutamic acid (mp. 71°-73° C.). An aliquot (1.3 g) of the compound, 0.46 g of L-proline methyl ester hydrochloride, 0.28 g of N-methylmorpholine and 0.51 g of N-hydroxybenzotriazole were dissolved in methylene chloride. Under ice cooling, 0.53 g of the water-soluble carbodiimide hydrochloride was added to the solution. The mixture was stirred for 30 minutes, and then further stirred overnight at room temperature. The resulting solution was washed successively with 5% aqueous potassium hydrogensulfate solution, aqueous sodium bicarbonate solution, and water, dried, and concentrated to dryness under reduced pressure to give an oily substance. The oily substance was purified by CHP20P column chromatography (40%→100% acetonitrile/water gradient) to give 1.4 g of a product. The product was dissolved in dioxane, and 6.5 ml of 1N-NaOH was added under cooling. The mixture was stirred at room temperature. After the reaction, the reaction mixture was adjusted to pH 2 to 3, and extracted with ethyl acetate. The extract was washed with aqueous sodium chloride solution, dried and concentrated to dryness under reduced pressure. Trifluoroacetic acid (10 ml) was added to the residue, and under ice cooling, the mixture was stirred for 30 minutes. Trifluoroacetic acid was evaporated under reduced pressure, and the residue was subjected to CHP20P column chromatography (0%→60% acetonitrile/water gradient). Fractions containing the desired product were concentrated to dryness and lyophilized to give 0.68 g of the captioned compound.

$[\alpha]_D^{25}$: −45.5° (1N-NaOH)

Elemental analysis for C$_{24}$H$_{34}$N$_4$O$_8$.H$_2$O: Calculated (%): C: 54.95, H: 6.92, N: 10.68. Found (%): C: 54.87, H: 6.74, N: 10.88.

EXAMPLES 79–83

The following compounds were synthesized in the same way as in Example 78:

2-[N$^2$-Benzyloxycarbonyl-L-lysyl-gamma-D-glutamyl]-1,2,3,4-tetrahydroisoquinoline-3(S)-carboxylic acid (Example 79):

$[\alpha]_D^{25}$: −11.9° (1N-NaOH)

Elemental analysis for C$_{29}$H$_{36}$N$_4$O$_8$.1.5H$_2$O: Calculated (%): C: 58.48, H: 6.60, N: 9.41. Found (%): C: 58.32, H: 6.71, N: 9.03.

N$^2$-Benzyloxycarbonyl-L-lysyl-gamma-D-glutamyl-N-cyclooctylglycine (Example 80):

$[\alpha]_D^{25}$: −16.0° (1N-NaOH)

Elemental analysis for C$_{29}$H$_{44}$N$_4$O$_8$.1.25H$_2$O: Calculated (%): C: 58.13, H: 7.82, N: 9.35. Found (%): C: 57.88, H: 7.76, N: 9.21.

2-(N$^2$-Benzyloxycarbonyl-L-lysyl-gamma-D-glutamyl)-cis-endo-2-azabicyclo[3.3.0]octane-3-carboxylic acid (Example 81):

$[\alpha]_D^{27}$: −10.7° (1N-NaOH)

Elemental analysis for C$_{27}$H$_{39}$N$_4$O$_8$.0.75H$_2$O: Calculated (%): C: 57.90, H: 7.11, N: 10.00. Found (%): C: 57.81, H: 7.08, N: 9.90.

N$^2$-Benzyloxycarbonyl-L-lysyl-gamma-D-glutamyl-N-cyclopentylglycine (Example 82):

$[\alpha]_D^{26}$: −14.2° (1N-NaOH)

Elemental analysis for C$_{26}$H$_{38}$N$_4$O$_8$.0.5H$_2$O: Calculated (%): C: 57.45, H: 7.23, N: 10.31. Found (%): C: 57.33, H: 7.24, N: 10.06.

3-(N$^2$-Benzyloxycarbonyl-L-lysyl-gamma-D-glutamyl)thiazolidine-4(R)-carboxylic acid (Example 83):

$[\alpha]_D^{27}$: −11.2° (1N-NaOH)

Elemental analysis for C$_{23}$H$_{32}$N$_4$O$_8$S.0.5H$_2$O.C$_4$H$_8$O$_2$: Calculated (%): C: 52.16, H: 6.55, N: 9.01, S: 5.16. Found (%): C: 52.01, H: 6.86, N: 8.79, S: 5.33,

EXAMPLE 84

Ethyl 1-(N$^2$-benzyloxycarbonyl-L-lysyl-gamma-D-glutamyl)indoline-2(S)-carboxylate Ethyl indoline-2(S)-carboxylate hydrochloride (11.6 g), 5.2 g of triethylamine and 19 g of alpha-benzyl N-benzyloxycarbonyl-D-glutamate were dissolved in 150 ml of methylene chloride, and 15.6 g of the water-soluble carbodiimide hydrochloride was added. The mixture was stirred overnight at room temperature. The reaction solution was washed successively with 10% hydrochloric acid, aqueous sodium bicarbonate solution and aqueous sodium chloride solution, and dried. The solvent was evaporated, and the residue was recrystallized from ethanol/ether to give 16.0 g of ethyl 1-(N-benzyloxycarbonyl-O$^1$-benzyl-gamma-D-glutamyl)indoline-2(S)-carboxylate (mp. 114°–116° C.).

An aliquot (5.0 g) of this ester was suspended in a mixture of 100 ml of methanol and 30 ml of water, and 5 ml of acetic acid, 4.6 g of ammonium formate and 0.5 g of 10% palladium-carbon were added to the suspension. The mixture was stirred at 50° C. for 1 hour. The catalyst was removed by filtration. The mother liquor was adjusted to pH 7 and concentrated. The residual solution was cooled. The precipitated crystals were collected by filtration and recrystallized from ethanol/water (1/1) to give 2.2 g of ethyl 1-(gamma-D-glutamyl)indoline-2(S)-carboxylate (mp. 197°–200° C., decomp.). An aliquot (2.0 g) of this ester and 0.66 g of sodium carbonate were dissolved in 25 ml of water, and a solution of 3.3 g of N$^2$-benzyloxycarbonyl-N$^6$-t-butoxycarbonyl-L-lysine N-hydroxysuccinimide ester in 25 ml of THF was added. The mixture was stirred overnight at room temperature. Tetrahydrofuran was evaporated, and 5% aqueous potassium hydrogensulfate solution was added. The precipitated crystals were collected by filtration and recrystallized from ethanol/ether to give 3.3 g of ethyl 1-(N$^2$-benzyloxycarbonyl-N$^6$-t-butoxycarbonyl-L-lysyl-gamma-D-glutamyl)indoline-2(S)-carboxylate. An aliquot (0.7 g) of this ester was stirred with 10 ml of trifluoroacetic acid under ice cooling for 20 minutes. The reaction mixture was concentrated to dryness under reduced pressure, and the residue was subjected to CHP20P column chromatography (0%→50% acetonitrile/water gradient). Fractions containing the desired product were concentrated, and the precipitated crystals were collected by filtration to give 0.34 g of the captioned compound.

Melting point: 188°–191° C.

$[\alpha]_D^{26}$: −63.9° (DMF)

Elemental analysis for C$_{30}$H$_{38}$N$_4$O$_8$.1.75H$_2$O: Calculated (%): C: 58.67, H: 6.81, N: 9.12. Found (%): C: 58.71, H: 6.84, N: 9.40.

EXAMPLE 85

The following compound was synthesized in the same way as in Example 84.

Ethyl (2S,3aS,7aS)-1-(N$^2$-benzyloxycarbonyl-L-lysyl-gamma-D-glutamyl)octahydro-1H-indole-2-carboxylate Elemental analysis for C$_{30}$H$_{44}$N$_4$O$_8$.1.75H$_2$O: Calculated (%): C: 58.10, H: 7.72, N: 9.03. Found (%): C: 58.07, H: 7.49, N: 8.98.

EXAMPLE 86

1-(N$^2$-Benzyloxycarbonyl-L-lysyl-O$^1$-ethyl-gamma-D-glutamyl)indoline-2(S)-carboxylic acid The water-soluble carbodiimide hydrochloride (4.3 g), 4.0 g of 1-benzyloxycarbonyl-indoline-2(S)-carboxylic acid, 1.2 g of t-butanol and 1.05 g of 4-dimethylaminopyridine were stirred in methylene chloride under ice cooling for 2 hours and then at room temperature overnight. The reaction mixture was washed successively with 10% citric acid, aqueous sodium bicarbonate solution and aqueous sodium chloride solution, and dried. The solvent was evaporated, and the residue was purified by silica gel column chromatography to give 4.4 g of t-butyl 1-benzyloxycarbonyl-indoline-2(S)-carboxylate as an oil. The resulting ester (4.0 g) was dissolved in a mixture of t-butanol, dioxane and methanol, and 5.7 g of ammonium formate and 0.5 g of 10% palladium-carbon were added. The mixture was stirred for 6 hours at room temperature. The catalyst was removed by filtration, and the solvent was evaporated. Aqueous sodium bicarbonate solution was added to the residue, and the mixture was extracted with ethyl acetate. The organic layer was washed with aqueous sodium chloride solution, and dried. The solvent was evaporated. The residue was mixed with 1.3 g of oxalic acid and recrystallized from ether/isopropanol to give 3.9 g of t-butyl indoline-2(S)-carboxylate oxalate (mp. 123°–125° C.). A methylene chloride solution of 2.6 g of t-butyl indoline-2(S)-carboxylate, 3.7 g of alpha-ethyl N-benzyloxycarbonyl-D-glutamate and 3.8 g of the water-soluble carbodiimide hydrochloride was stirred at room temperature for 4 hours. The reaction mixture was washed successively with aqueous sodium bicarbonate solution, 5% aqueous potassium hydrogensulfate solution, and dried. The solvent was evaporated, and the residue was recrystallized from n-hexane/ethanol to give 4.0 g of t-butyl 1-(N-benzyloxycarbonyl-O$^1$-ethyl-gamma-D-glutamyl)indoline-2(s)-carboxylate. This product was dissolved in ethanol and 2.6 g of ammonium formate and 1.0 g of 10% palladium-carbon were added. The mixture was stirred at room temperature for 6 hours. The catalyst was removed by filtration, and the solvent was evaporated. The residue was mixed with aqueous sodium bicarbonate solution and extracted with ethyl acetate. The organic layer was washed with water, and dried. The solvent was evaporated to give 2.6 g of an oily substance. An aliquot (2.4 g) of the oily substance, 2.67 g of N$^2$-benzyloxycarbonyl-N$^6$-t-butoxycarbonyl-L-lysine and 2.08 g of the water-soluble carbodiimide hydrochloride were stirred in methylene chloride for 2 hours. The reaction mixture was washed successively with aqueous sodium bicarbonate solution and 5% aqueous potassium hydrogensulfate solution and dried. The solvent was evaporated to give 4.7 g of a glassy substance. An aliquot (0.7 g) of the glassy substance was stirred with 10 ml of trifluoroacetic acid under ice cooling for 10 minutes. The mixture was concentrated to dryness under reduced pressure, and the residue was subjected to CHP20P column chromatography. Fractions containing the desired product were concentrated to give 0.24 g of the captioned compound.

Melting point: 207°–212° C.

$[\alpha]_D^{26}$: −3.2° (DMF)

Elemental analysis for $C_{30}H_{38}N_4O_8 \cdot 0.75H_2O$: Calculated (%): C: 60.44, H: 6.68, N: 9.40. Found (%): C: 60.63, H: 6.54, N: 9.43.

EXAMPLE 87

|  | per 1,000 tablets |
|---|---|
| (2S,3aS,7aS)-1-(N$^2$—nicotinoyl-L-lysyl-gamma-D-glutamyl)octahydro-1H—indole-2-carboxylic acid | 25 g |
| Corn starch | 28 g |
| Lactose | 60 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and compressed into 1,000 tablets each weighing 150 mg by a conventional method. The tablets were further coated with hydroxypropyl methylcellulose, talc, titanium dioxide, and sorbitan fatty acid ester in a customary manner. There were obtained 1,000 coated tablets.

EXAMPLE 88

|  | per 1,000 tablets |
|---|---|
| (2S,3aS,7aS)-1-(N$^2$—nicotinoyl-L-lysyl-gamma-D-glutamyl)octahydro-1H—indole-2-carboxylic acid | 100 g |
| Corn starch | 66 g |
| Lactose | 50 g |
| Microcrystalline cellulose | 30 g |
| Light anhydrous silicic acid | 2 g |
| Magnesium stearate | 2 g |

The above components were blended, granulated and filled into 1,000 capsules by a conventional method.

EXAMPLE 89

The same procedures as in Examples 87 and 88 were repeated except that (2S,3aS,7aS)-1-[N$^2$-(4-hydroxybenzoyl)-L-lysyl-gamma-D-glutamyl]octahydro-1H-indole-2-carboxylic acid was used in place of (2S,3aS,7aS)-1-(N$^2$-nicotinoyl)-L-lysyl-gamma-D-glutamyl]octahydro-1H-indole-2-carboxylic acid. Thus tablets and capsules were prepared respectively.

The following compounds can be synthesized as in the foregoing Examples.

(2S,3aS,7aS)-1-[N$^2$-(4-Hydroxyphenylethoxycarbonyl)-L-lysyl-gamma-D-glutamyl]octahydro-1H-indole-2-carboxylic acid (as in Example 26).

1-{N$^2$-[(5-Hydroxypyridin-2-yl)methoxycarbonyl]-L-lysyl-gamma-D-glutamyl}indoline-2(S)-carboxylic acid (as in Example 38).

1-{N$^2$-[(5-Methoxypyridin-2-yl)methoxycarbonyl]-L-lysyl-gamma-D-glutamyl}indoline-2(S)-carboxylic acid (as in Example 38).

(2S,3aS,7aS)-1-{N$^2$-[(3-Chloropyridin-2-yl)methoxycarbonyl]-L-lysyl-gamma-D-glutamyl}octahydro-1H-indole-2-carboxylic acid (as in Example 27).

(2S,3aS,7aS)-1-{N$^2$-[(3-Methylpyridin-2-yl)methoxycarbonyl]-L-lysyl-gamma-D-glutamyl}octahydro-1H-indole-2-carboxylic acid (Example 27).

(2S,3aS,7aS)-1-[N$^2$-(Cyclopentylcarbonyl)-L-lysyl-gamma-D-glutamyl]octahydro-1H-indole-2-carboxylic acid (as in Example 18).

(2S,3aS,7aS)-1-[N$^2$-(4-iso-Propylbenzyloxycarbonyl)-L-lysyl-gamma-D-glutamyl]octahydro-1H-indole-2-carboxylic acid (as in Example 51).

1-[N$^2$-(4-Dimethylaminobenzoyl)-L-lysyl-gamma-D-glutamyl]indole-2(S)-carboxylic acid (as in Example 51).

(2S,3aS,7aS)-1-{N$^2$-[(2-Methylpyridin-5-yl)carbonyl]-L-lysyl-gamma-D-glutamyl}octahydro-1H-indole-2-carboxylic acid (as in Example 15).

(2S,3aS,7aS)-1-{N$^2$-[(2-Hydroxypyridin-5-yl)carbonyl]-L-lysyl-gamma-D-glutamyl}octahydro-1H-indole-2-carboxylic acid (as in Example 15).

1-{N$^2$-[(2-Pyrrolidinylpyridin-5-yl)carbonyl]-L-lysyl-gamma-D-glutamyl}indole-2-carboxylic acid (as in Example 15).

(2S,3aS,7aS)-1-{N$^2$-[(2-Morpholinylpyridin-5-yl)carbonyl]-L-lysyl-gamma-D-glutamyl}octahydro-1H-indole-2-carboxylic acid (as in Example 15).

1-{N$^2$-[(2-Dimethylaminopyridin-5-yl)-L-lysyl-gamma-D-glutamyl}indole-2-carboxylic acid (as in Example 15).

What is claimed is:

1. A tripeptide derivative of the following formula $$\begin{array}{c} T\!\!-\!\!(CH_2)_{\overline{m}}\!-\!NH_2 \\ | \\ CH_2 \qquad\qquad COOR_2 \\ | \qquad\qquad\qquad | \\ R_1\!-\!W\!-\!CO\!-\!NH\!-\!CH\!-\!CO\!-\!NH\!-\!CH\!-\!(CH_2)_{\overline{2}}\!-\!CO\!-\!R_3 \end{array} \qquad (I)$$

wherein R$_1$ is a C$_{1-10}$ alkyl group, a C$_{4-7}$ cycloalkyl or C$_{5-7}$ cycloalkyl-lower alkyl group, a phenyl or phenyl-lower alkyl group in which the benzene ring is unsubstituted or is substituted by a substituent selected from the group consisting of halogen, lower alkyl, lower alkoxy, phenyl, methylenedioxy, ethylenedioxy, amino, di(-lower alkyl) amino and hydroxy, a naphthyl or naphthyl-lower alkyl group in which the naphthalene ring is unsubstituted or is substituted by a substituent selected from the group consisting of halogen, lower alkyl, lower alkoxy and hydroxy, a heterocyclic or heterocyclic-lower alkyl group is which the heterocycle is a saturated or unsaturated 5- or 6-membered ring containing a nitrogen, oxygen or sulfur atom as the hetero atom, and is unsubstituted or is substituted by a substituent selected from the group consisting of halogen, lower alkyl, lower alkoxy, amino, di(lower alkyl)amino, hydroxy, oxo and saturated 5- or 6-membered nitrogen-containing heterocylic group, and is unfused or is fused to a benzene ring, or an imidazolylvinyl group; $R_2$ is a hydrogen atom, a $C_{1-10}$ alkyl group or a benzyl group; $R_3$ is a group of the formula

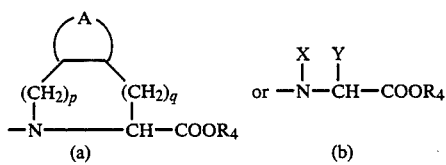

in which 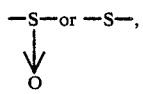

is a benzene, cyclopentane or cyclohexane ring, $R_4$ is a hydrogen atom, a $C_{1-10}$ alkyl group or a benzyl group, p is 0 or 1, q is 1, 2, or 3, and X is a phenyl group which is unsubstituted or is substituted by a substituent selected from the group consisting of halogen, lower alkoxy and hydroxy, a $C_{4-8}$ cycloalkyl group, or a $C_{5-7}$ cycloalkyl group which is fused to a benzene, and Y is a hydrogen atom or a lower alkyl group, or X and Y, together with the nitrogen and carbon atoms to which they are bonded, forms a 5- or 6-membered heterocycle which may contain a nitrogen, oxygen or sulfur atom, W is a single bond, —O— or —NH—, T is a single bond,

and m is 2 or 3,
or salts thereof.

2. The compound of claim 1 wherein W is a single bond or —O— and T is a single bond.

3. The compound of claim 1 wherein $R_2$ and $R_4$ are both hydrogen atoms.

4. The compound of claim 1 wherein $R_3$ represents the group of formula (a) in which

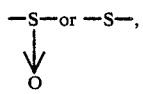

represents a benzene or cyclohexane ring, p is 0 and q is 1.

5. The compound of claim 1 which is a tripeptide derivative represented by the following formula

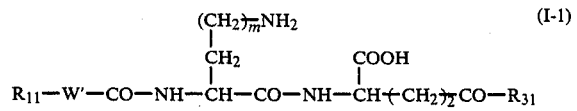

wherein $R_{11}$—W'— represents a $C_{4-7}$ cycloalkyl, $C_{4-7}$ cycloalkyloxy, cyclohexylmethyloxy or cyclohexylethyloxy group, a phenyl group which may optionally be substituted by a substituent selected from lower alkoxy, halogen and hydroxy, a benzyloxy or phenethyloxy group in which the benzene ring may optionally be substituted by a substituent selected from lower alkoxy, methylenedioxy and hydroxy, a pyridyl group which may optionally be substituted, preferably at the 2- or 6-position, by a substituent selected from halogen, lower alkoxy, methyl and dimethylamino, a pyridymethyloxy or pyridylethyloxy group in which the pyridine ring may optionally be substituted, preferably at the 3- or 6-position, by a substituent selected from methoxy and hydroxy, a 2-indolinyl, 2-pyrrolidinyl, 2-pyrazinyl, 2-furyl, 2-thienyl or 3-quinolyl group, or a 4-imidazolylvinyl group; $R_{31}$ represents a 2(S)-carboxyindolinyl or 2-carboxy(2S,3aS,7aS)octahydro-indolyl group; and m is 2 or 3,
or a salt thereof.

6. The compound of claim 1 which is a tripeptide derivative represented by the following formula

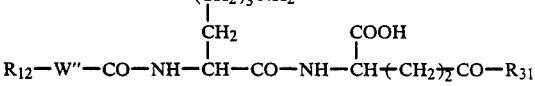

wherein $R_{12}$—W'''— represents a cyclobutyl, cyclopentyl, cyclobutyloxy or cyclopentyloxy group, a phenyl group which may optionally be substituted, at the 2- or 4-position, by a substituent selected from lower alkoxy and hydroxy, a phenethyloxy group which may optionally be substituted by hydroxy at the 4-position of the benzene ring, or a pyridyl group which may optionally be substituted by halogen or lower alkyl; and $R_{31}$ represents a 2(S)-carboxyindolinyl or 2-carboxy(2S,3aS,7aS)octahydro-indolyl group,
or a salt thereof.

7. The compound of claim 6 which is (2S,3aS,7aS)-1-($N^2$-pyridylcarbonyl-L-lysyl-gamma-D-glutamyl)octahydro-1H-indole-2-carboxylic acid or 1-($N^2$-pyridylcarbonyl-L-lysyl-gamma-D-glutamyl)indoline-2(S)-carboxylic acid or a salt thereof.

8. The compound of claim 6 which is (2S,3aS,7aS)-1-[$N^2$-(nicotinoyl)-L-lysyl-gamma-D-glutamyl)octahydro-1H-indole-2-carboxylic acid or 1-($N^2$-nicotinoyl-L-lysyl-gamma-D-glutamyl)indoline-2(S)-carboxylic acid or a salt thereof.

9. The compound of claim 6 which is (2S,3aS,7aS)-1-[$N^2$-(2- or 4-hydroxy- or 2- or 4-$C_{1-3}$ alkoxy-substituted benzoyl)-L-lysyl-gamma-D-glutamyl)octahydro-1H-indole-2-carboxylic acid or 1-[$N^2$-2- or 4-hydroxy- or 2- or 4-$C_{1-3}$-alkoxy-substituted benzoyl)-L-lysyl-gamma-D-glutamyl)indoline-2-(S)-carboxylic acid.

10. The compound of claim 9 which is (2S,3aS,7aS)-1-[$N^2$-(4-hydroxybenzoyl)-L-lysyl-gamma-D-glutamyl]octahydro-1H-indole-2-carboxylic acid or 1-[$N^2$-(4-hydroxybenzoyl)-L-lysyl-gamma-D-glutamyl)indoline-2(S)-carboxylic acid or a salt thereof.

11. The compound of claim 1 wherein the configuration of the carbon atom at the alpha-position of the basic amino acid moiety is L, the configuration of the carbon atom at the alpha-position of the glutamic acid moiety is D, and the configuration of the carbon atom to which —COOR$_4$ is bonded in the group $R_3$ is S.

12. The compound of claim 11 which is (2S,3aS,7aS)-1-(N²-nicotinoyl-L-lysyl-gamma-D-glutamyl)octahydro-1H-indole-2-carboxylic acid or its salt.

13. The compound of claim 11 which is (2S,3aS,7aS)-1-[N²-(4-hydroxybenzoyl)-L-lysyl-gamma-D-glutamyl)octahydro-1H-indole-2-carboxylic acid or its salt.

14. A pharmaceutical composition comprising a tripeptide derivative of formula (I) or its pharmaceutically acceptable salt according to claim 1 and a pharmaceutically acceptable carrier or diluent.

15. A pharmaceutical composition comprising a tripeptide derivative of formula (I) or its pharmaceutically acceptable salt according to claim 1, a diuretic agent and a pharmaceutically acceptable carrier or diluent.

16. A method of treating hypertension in a hypertensive patient, which comprises administering an antihypersensitively effective amount of a tripeptide derivative of formula (I) or its pharmaceutically acceptable salt to the patient.

17. The method of claim 16 wherein a diuretic agent is co-administered with a tripeptide derivative of formula (I) or its pharmaceutical acceptable salt.

* * * * *